(12) United States Patent
Lazarev

(10) Patent No.: US 10,163,575 B1
(45) Date of Patent: Dec. 25, 2018

(54) NON-LINEAR CAPACITOR AND ENERGY STORAGE DEVICE COMPRISING THEREOF

(71) Applicant: Capacitor Sciences Incorporated, Menlo Park, CA (US)

(72) Inventor: Pavel Ivan Lazarev, Menlo Park, CA (US)

(73) Assignee: CAPACITOR SCIENCES INCORPORATED, Menlo Park, CA (US)

( * ) Notice: Subject to any disclaimer, the term of this patent is extended or adjusted under 35 U.S.C. 154(b) by 0 days.

(21) Appl. No.: 15/806,194

(22) Filed: Nov. 7, 2017

(51) Int. Cl.
*H01G 7/06* (2006.01)
*C07D 471/22* (2006.01)
(Continued)

(52) U.S. Cl.
CPC ............ *H01G 7/06* (2013.01); *C07D 471/06* (2013.01); *C07D 471/22* (2013.01); *C08F 20/36* (2013.01); *C08F 20/60* (2013.01); *C08F 20/68* (2013.01)

(58) Field of Classification Search
CPC ...... H01G 7/06; C07D 471/06; C07D 471/22; C08F 20/36; C08F 20/60; C08F 20/68
(Continued)

(56) References Cited

U.S. PATENT DOCUMENTS 6,341,056 B1    1/2002   Allman et al.
7,211,824 B2    5/2007   Lazarev
(Continued)

FOREIGN PATENT DOCUMENTS

WO    2015175522 A1    11/2015

OTHER PUBLICATIONS

Hindawi Publishing Corporation, Khalil Ahmed et al., "High dielectric constant polyaniline/poly(acrylic acid) composites prepared by in situ polymerization", pp. 630-637, University of the Punjab, New Campus, Lahore 54590, Oct. 17, 2015.
(Continued)

*Primary Examiner* — Michael P McFadden
(74) *Attorney, Agent, or Firm* — JDI Patent; Joshua Isenberg; Robert Pullman

(57) ABSTRACT

The present disclosure provides a non-linear capacitor comprising a first electrode, a second electrode, and a dielectric layer disposed between said first and second electrodes. The dielectric layer comprises at least one organic compound selected from copolymer, homo-polymer, Sharp polymers, NLSD compounds and combination thereof which have at least one electro-polarizable aromatic polycyclic conjugated core. A relationship between a capacity C of the capacitor and a voltage V between the electrodes is characterized by the monotonously increasing polynomial dependence $C_0 + \sum_{i=1}^{m} C_i V^i$, when the voltage V satisfies by following inequality $0 < V \leq V_{max}$, where the voltage $V_{max}$ is a maximum working voltage that does not exceed a breakdown voltage $V_{bd}$ and which is selected out of safety reasons, where at least one coefficient $C_i$ is not equal to 0 when the index i ranges from 2 to m, and m=2, 3, 4, 5, or 6.

15 Claims, 5 Drawing Sheets

(51) Int. Cl.
*C07D 471/06* (2006.01)
*C08F 20/36* (2006.01)
*C08F 20/60* (2006.01)
*C08F 20/68* (2006.01)

(58) Field of Classification Search
USPC ........................................................ 361/277
See application file for complete search history.

(56) References Cited

U.S. PATENT DOCUMENTS

| | | | |
|---|---|---|---|
| 8,222,074 | B2 | 7/2012 | Lazarev |
| 8,552,179 | B2 | 10/2013 | Lazarev |
| 9,293,260 | B2 | 3/2016 | Schmid et al. |
| 9,589,727 | B2 | 3/2017 | Lazarev |
| 2003/0103319 | A1 | 6/2003 | Kumar et al. |
| 2004/0222413 | A1 | 11/2004 | Hsu et al. |
| 2006/0120014 | A1 | 6/2006 | Nakamura et al. |
| 2006/0120020 | A1 | 6/2006 | Dowgiallo |
| 2007/0001258 | A1 | 1/2007 | Aihara |
| 2008/0002329 | A1 | 1/2008 | Pohm et al. |
| 2008/0266750 | A1 | 10/2008 | Wu et al. |
| 2010/0038629 | A1 | 2/2010 | Lazarev |
| 2010/0214719 | A1 | 8/2010 | Kim et al. |
| 2010/0309606 | A1 | 12/2010 | Allers et al. |
| 2012/0122274 | A1 | 5/2012 | Lazarev |
| 2014/0145550 | A1* | 5/2014 | Hitchcock ............. H01L 41/113 310/300 |
| 2016/0020026 | A1 | 1/2016 | Lazarev |
| 2016/0020027 | A1 | 1/2016 | Lazarev |
| 2016/0254092 | A1 | 9/2016 | Lazarev et al. |
| 2016/0314901 | A1 | 10/2016 | Lazarev |
| 2016/0340368 | A1 | 11/2016 | Lazarev |
| 2016/0379757 | A1 | 12/2016 | Robinson et al. |
| 2017/0117097 | A1 | 4/2017 | Furuta et al. |
| 2017/0233528 | A1 | 8/2017 | Sharp et al. |
| 2017/0236648 | A1 | 8/2017 | Lazarev et al. |
| 2017/0237271 | A1 | 8/2017 | Kelly-Morgan et al. |
| 2017/0237274 | A1 | 8/2017 | Lazarev et al. |
| 2017/0287637 | A1 | 10/2017 | Lazarev et al. |
| 2017/0287638 | A1 | 10/2017 | Lazarev et al. |

OTHER PUBLICATIONS

International Union of Pure and Applied Chemistry Polymer Divison Stejskal et al., "Polyaniline: Thin Films and Colloidal Dispersions (IUPAC Technical Report)", vol. 77, No. 5, pp. 815-826, Russian Academy of Sciences, St. Petersburg 199004, Russia; 2005.

Roger D. Hartman and Herbert A. Pohl, "Hyper-electronic Polarization in Macromolecular Solids", Journal of Polymer Science: Part A-1, vol. 6, pp. 1135-1152 (1968).

* cited by examiner

NON-LINEAR CAPACITOR AND ENERGY STORAGE DEVICE COMPRISING THEREOF

FIELD OF THE INVENTION

The present invention relates generally to passive components of electrical circuit and more particularly to a non-linear capacitor and an energy storage device comprising thereof.

BACKGROUND

Energy storage is a crucial component of a large number and variety of electronic devices, particularly mobile devices and vehicles, such as electric and hybrid gas-electric vehicles (also "hybrid vehicles" herein). Energy storage devices can be based on a variety of physical effects. For example, electric fields can be employed to store energy in capacitors, and chemical reactions (involving ion motion) can be employed to store energy in batteries. However, energy storage in a capacitor can be limited by the geometry of current devices (e.g., 2-D capacitor plates having limited surface areas) and either a low permittivity or low dielectric breakdown voltage, and batteries can have a slow response time due to the relatively slow ion motion inherent in electrochemical reactions.

There are limitations associated with current batteries. For example, current batteries can have low storage densities due to the relatively low voltage (<5V) resulting from the electrochemical reactions of the ions. In addition, the low mobility of ions in current batteries can lead to slow charge and discharge performance. Furthermore, the reliance of existing batteries on ionic transport causes high degradation rates of the batteries. The performance of battery powered devices, such as hybrid or electric vehicles, can be limited by the low energy stored per weight of batteries used in such vehicles.

An important characteristic of a dielectric material is its dielectric permittivity. Different types of dielectric materials are used for capacitors and include ceramics, polymer film, paper, and electrolytic capacitors of different kinds. The most widely used polymer film materials are polypropylene and polyester. Increasing dielectric permittivity allows for increasing volumetric energy density, which makes it an important technical task.

Second-order nonlinear optical (NLO) effects of organic molecules have been extensively investigated for their advantages over inorganic crystals. Properties studied, for example, include their large optical non-linearity, ultra-fast response speed, high damage thresholds and low absorption loss, etc. Particularly, organic thin films with excellent optical properties have tremendous potential in integrated optics such as optical switching, data manipulation and information processing. Among organic NLO molecules, azo-dye chromophores have been a special interest to many investigators because of their relatively large molecular hyper-polarizability (b) due to delocalization of the p-electronic clouds. They were most frequently either incorporated as a guest in the polymeric matrix (guest-host polymers) or grafted into the polymeric matrix (functionalized polymers) over the past decade.

Hyper-electronic polarization of organic compounds is described in greater detail in Roger D. Hartman and Herbert A. Pohl, "Hyper-electronic Polarization in Macromolecular Solids", Journal of Polymer Science: Part A-1 Vol. 6, pp. 1135-1152 (1968). Hyper-electronic polarization may be viewed as the electrical polarization external fields due to the pliant interaction with the charge pairs of excitons, in which the charges are molecularly separated and range over molecularly limited domains. In this article four polyacene quinone radical polymers were investigated. These polymers at 100 Hz had dielectric constants of 1800-2400, decreasing to about 58-100 at 100,000 Hz. Essential drawback of the described method of production of material is use of a high pressure (up to 20 kbars) for forming the samples intended for measurement of dielectric constants.

Copolymers of methyl methacrylate with a methacrylate containing a rigid group with two azo bonds (3RM) were prepared and their photoinduced birefringence levels and rates studied in X. Meng, A. Natansohn and P. Rochon, "Azo polymers for reversible optical storage: 13. Photoorientation of rigid side groups containing two azo bonds", *Polymer* Vol. 38 No. 11, pp. 2677-2682, (1997). Birefringence levels of 0.11 for the copolymer with 11.6 mol % azo structural units and 0.13 for the copolymer with 30.0 mol % azo structural units were found; this is higher than the birefringence inducible in a typical azo homopolymer containing a chromophore with only one azo group, poly{4'-[(2-(acryloyloxy) ethyl)ethylamino]-4-nitroazobenzene} [poly(DR1A)]. The birefringence per azo structural unit for a copolymer containing 11.6 mol % 3RM is about five times that for a DR1A copolymer with similar azo content, because of the intrinsic structural properties of 3RM (high length/diameter ratio). Dichroism in both u.v. and visible regions of the spectrum contribute to the overall photoinduced birefringence. The rate of inducing birefringence in the 3RM copolymers is lower than in poly(DR1A) and the birefringence stability (91-96% of the induced birefringence is maintained after the writing laser is off) is much better than that for poly(DR1A) (about 80%). The good stability and slow birefringence growth rate are due to the lesser mobility of the larger side group. Novel polymers with azobenzene moiety with alkyl spacer and different substituents units are presented in VitaliySmokal, Oksana Krupka, Agnesa Sinugina, and Vladimir Syromyatnikov, "Synthesis, Characterization, and Study of Novel Push-Pull Azobenzene Polymers", *Mol. Cryst. Liq. Cryst.*, Vol. 590: pp. 105-110, (2014). Azopolymers were obtained by a two-step synthetic approach. This includes the preparation of a methacrylic monomers and their polymerization. Their photophysical and photochemical properties have been investigated. Polymers were characterized and evaluated by 1HNMR, IR, UV spectroscopy. Thermal stability was characterized by DSC method. The synthesized polymers exhibited glasstransition temperatures in the range of 110-140° C.

The second- and third-order nonlinear optical response of spin-deposited thin films of three different push-pull side chain azobenzene polymers is investigated by the second- and third-harmonic Maker fringes techniques using 30 ps laser pulses at a fundamental wavelength of 1064 nm in Hasnaa El Ouazzani et. al., "Second- and Third-Order Nonlinearities of Novel Push-Pull Azobenzene Polymers", J. Phys. Chem. B, vol. 115, pp. 1944-1949 (2011). Measurements were carried out before and after aligning the chromophores by corona poling of the films, while different polarization configurations have been utilized. Strong dependence of the response upon the structure of the systems has been found, which is related to the different charge transfer within the molecules. The reported findings are compared with already published results.

The synthesis of side chain methacrylic polymers functionalized with azobenzene chromophores is described in greater detail in Oksana Krupka et. al., "ELECTRO-OPTICAL PROPERTIES IN THIN FILMS OF NEW AZOBEN- ZENE POLYMERS", *CHEMISTRY & CHEMICAL TECHNOLOGY*, Vol. 9, No. 2, pp. 137-141, (2015). A reversible change of thin film absorption is observed when illuminating it with monochromatic, linearly polarized light under the applied external DC field. The amount of change depends on the angle between the light polarization and the DC electric field direction.

It is known that energy storage device based on capacitor have well-known advantages versus with electrochemical energy storage device, e.g. a battery. However, an ordinary energy storage device based on capacitor often do not store energy in small volume or weight as in case of a battery, or at low energy storage cost, which makes capacitors impractical for some applications, for example electric vehicles. Compared to batteries, disclosed solid state energy storage device is able to store energy with very high power density, i.e. charge/recharge rates, have long shelf life with little degradation, and can be charged and discharged (cycled) hundreds of thousands or millions of times.

SUMMARY

The present disclosure provides a non-linear capacitor comprising a first electrode, a second electrode, and a dielectric layer disposed between said first and second electrodes. The dielectric layer comprises at least one organic compound selected from copolymer, homo-polymer, Sharp polymers, NLSD compounds and combination thereof which have at least one electro-polarizable aromatic polycyclic conjugated core. A relationship between a capacity C of the capacitor and a voltage V between the electrodes is characterized by the monotonously increasing polynomial dependence $C_0 + \Sigma_{i=1}^{m} C_i V^i$, wherein the voltage V satisfies the following inequality $0 < V \leq V_{max}$, where the voltage $V_{max}$ is a maximum working voltage that does not exceed breakdown voltage $V_{bd}$ and which is selected out of safety reasons, where at least one coefficient $C_i$ is not equal to 0 for values of i ranging from 2 to m, and m=2, 3, 4, 5, or 6.

In another aspect, the present disclosure provides an energy storage device comprising the non-linearcapacitor with a power-law dependence of capacitance on voltage disclosed above, and which uses power electronics in the voltage range from $V_{max}$ 200 volts to about $V_{max}$ 1000 volts. In some instances, the energy storage device may operate at a $V_{max}$ greater than 1000 volts.

INCORPORATION BY REFERENCE

All publications, patents, and patent applications mentioned in this specification are herein incorporated by reference to the same extent as if each individual publication, patent, or patent application was specifically and individually indicated to be incorporated by reference.

Said organic compound may incorporate Sharp polymers commonly described in U.S. patent application Ser. No. 15/043,247 filed Feb. 12, 2016; YanLi polymers commonly described in U.S. patent application Ser. No. 15/449,587 filed Mar. 3, 2017, U.S. patent application Ser. No. 15/710, 587 filed Sep. 9, 2017; non-linear dielectric materials commonly described in U.S. patent application Ser. No. 15/469, 126 filed Mar. 24, 2017; electro-polarizable compounds commonly described in U.S. patent application Ser. No. 15/090,509 filed Apr. 4, 2016 U.S. patent application Ser. No. 15/163,595 filed May 24, 2016 which are incorporated herein by reference, describe exemplary composite polarizable organic compounds, which are herein referred to as electro-polarizable aromatic polycyclic conjugated cores.

BRIEF DESCRIPTION OF THE DRAWING

A more complete assessment of the present invention and its advantages will be readily achieved as the same becomes better understood by reference to the following detailed description, considered in connection with the accompanying drawings and detailed specification, all of which forms a part of the disclosure. Embodiments of the invention are illustrated, by way of example only, in the following Figures, of which.

DETAILED DESCRIPTION

Figure 1:
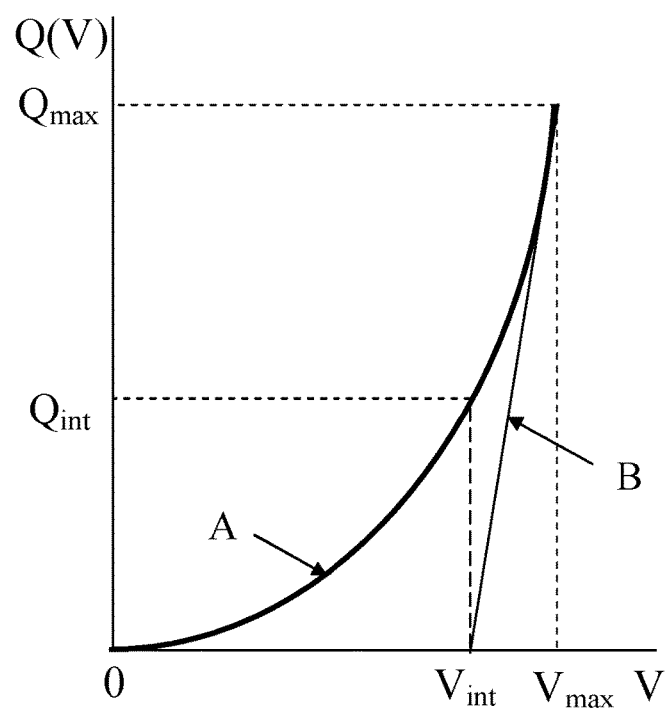
FIG. 1 schematically shows a relation between a charge Q on the electrodes of the capacitor and a voltage V applied to the electrodes.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure provides the non-linear capacitor as disclosed above. In one embodiment of the non-linear capacitor, the working range of voltage is from $V_{int}$ to $V_{max}$ where $V_{int}$ is determined by the intersection the straight line that is tangent to the dependence $Q(V)=C(V) \cdot V$ at the point $V=V_{max}$ with the abscissa axis, and the difference between voltages $V_{max}$ and $V_{int}$ is defined by the following ratio:

$$V_{max} - V_{int} = \frac{Q(V_{max})}{\frac{dQ}{dV}\bigg|_{V_{max}}}$$

In another embodiment of the present disclosure, the electro-polarizable aromatic polycyclic conjugated cores interact with each other due to dipole and π-π interactions and form molecular stacks, and the organic compound further comprises alkyl tail-substituents which are bonded to the polymer backbone or to conjugated Sharp and NLSD molecular compounds. The alkyl tail-substitutes interact with each other due to hydrophobic interaction and also form isolating cover round the molecular stacks, provide solubility of the organic compound, and preclude an avalanche breakdown of the dielectric layer at the working voltage applied to the electrodes of the capacitor. In yet another embodiment of the present disclosure, the electro-polarizable aromatic polycyclic conjugated core comprises benzene rings bonded with linker groups and is described by following structure formula:

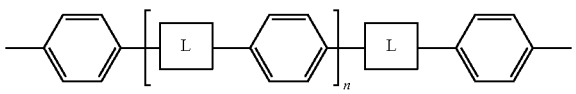

where L is linker group which is selected from —N═N—, —CC— (alkyne) and —CH═CH— and n=0, 1, 2, 3, 4, 5, and 6. In still another embodiment of the present disclosure, the electro-polarizable aromatic polycyclic conjugated core further comprises electrophilic groups (acceptors) and/or nucleophilic groups (donors) located in apex positions and/or in side (lateral) positions. The electrophilic groups (acceptors) are selected from —$NO_2$, —$NH_3^+$ and —NRR'R" (quaternary nitrogen salts), counterion $Cl^-$ or $Br^-$, —CHO (aldehyde), —CRO (keto group), —$SO_3H$ (sulfonic acids), —$SO_3R$ (sulfonates), $SO_2NH_2$ (sulfonamides), —COOH (carboxylic acid), —COOR (esters, from carboxylic acid side), —COCl (carboxylic acid chlorides), —CONH2 (amides, from carboxylic acid side), —$CF_3$, —$CCl_3$, —CN, wherein R is radical selected from the list comprising alkyl (methyl, ethyl, isopropyl, tert-butyl, neopentyl, cyclohexyl etc.), allyl (—CH2-CH═CH2), benzyl (—CH2C6H5) groups, phenyl (+substituted phenyl) and other aryl (aromatic) groups and where R' R" are independently selected for list of R radicals. The nucleophilic groups (donors) are selected from —$O^-$ (phenoxides, such as —ONa or —OK), —$NH_2$, —NHR, $NR_2$, —OH, —OR (ethers), —NHCOR (amides, from amine side), —OCOR (esters, from alcohol side), alkyls, —$C_6H_5$, vinyls, —NRR' wherein R and R' are radicals independently selected from the list comprising alkyl (methyl, ethyl, isopropyl, tert-butyl, neopentyl, cyclohexyl etc.), allyl (—CH2-CH═CH2), benzyl (—CH2C6H5) groups, phenyl (+substituted phenyl) and other aryl (aromatic) groups.

Existence of the electrophilic groups (acceptors) and the nucleophilic groups (donors) in the aromatic polycyclic conjugated molecule promotes non-uniform distribution of electronic density in the conjugated molecule: surplus of electrons in one place (in a donor zone) and a shortage of electrons in other place (in an acceptor zone). The influence of an external electric field on a non-uniform distribution of electronic density along the conjugated molecule leads to an induced polarization $P_{ind}$. In the general case the induced polarization is a nonlinear function of intensity of the local electric field $E_{loc}$. In the assumption of weak nonlinearity it is possible to approximate the induced polarization $P_{ind}$ by a few terms of a decomposition of the induced polarization into a series of degrees of intensity of a local electric field. In such situations the induced polarization of the environment (e.g., of a molecule) can be written down in the following form:

$$P_{ind} = \alpha \cdot E_{loc} + \beta \cdot E_{loc}^2 + \ldots ,$$

where α-linear polarizability, β-square polarizability. Though the assumption of a smallness of electric field is not always right, nevertheless parameters α and β may be used for qualitative analysis of polarizability of the disclosed compounds. In the present disclosure the main attention is paid to ways of increase in the induced polarization of the disclosed compounds and therefore onto ways of increase of the linear polarizability α and square polarizability β. Such attention is caused by that the constant dipole and quadrupole electrical moments are mutually neutralized at self-assembly of such conjugated molecules. The analysis shows that linear polarizability depends on the size of average electronic density in the molecule, and nonlinear polarizability depends on the size of heterogeneity of electronic density. It is also shown that a non-centrosymmetric arrangement of the electron donor and acceptor groups can lead to a strong nonlinear response of the compound's electronic polarization in the presence of an electric field. Influence of chemical structure on linear polarizability α and square polarizability β is shown in Table 1.

TABLE 1

Examples of the chemical structure with linear polarizability α and square polarizability β

| chemical structure | α | β |
|---|---|---|
| 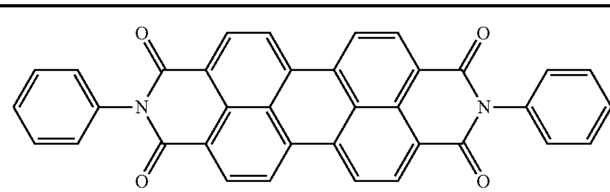 | 945 | 0.041 |
| 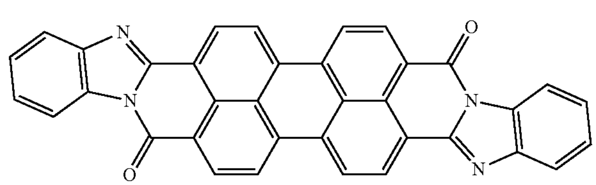 [SMILES: O=c1c2ccc3c4ccc5c6c(ccc(c7ccc(c2c37)c2nc3ccccc3n12)c46)c(=O)n1c2ccccc2nc51] | 1348 | 0.165 |

TABLE 1-continued

Examples of the chemical structure with linear polarizability α and square polarizability β

| chemical structure | α | β |
|---|---|---|
| *(structure)* | 1537 | 862 |
| *(structure)* | 1252 | 21107 |
| *(structure)* | 1908 | 40221 |
| *(structure)* | 1431 | 35189 |
| *(structure)* | 2057 | 168081 |

TABLE 1-continued

Examples of the chemical structure with linear polarizability α and square polarizability β

| chemical structure | α | β |
|---|---|---|
| 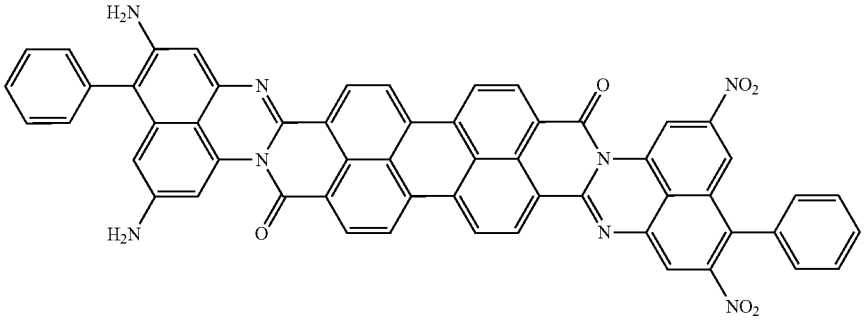 [SMILES: Nc1cc2c(-c3ccccc3)c(N)cc3nc4c5ccc6c7ccc8c(=O)n9c%10cc([N+](=O)[O-])cc%11c(-c%12ccccc%12)c([N+](=O)[O-])cc(nc9c9ccc(c%12ccc(c(=O)n4c(c1)c32)c5c6%12)c7c89)c%11%10] | 3397 | 582843 |
| 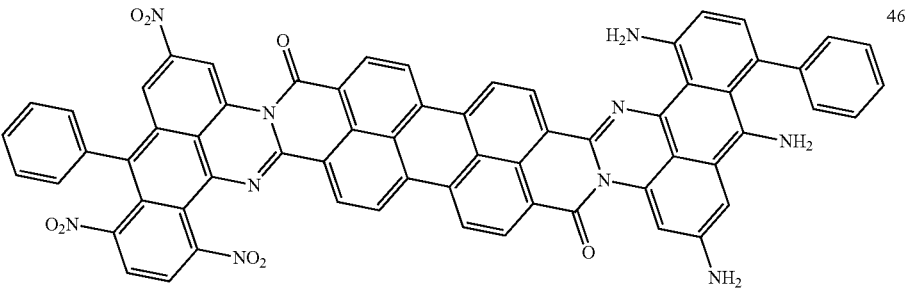 | 4604 | 1002570 |

Table 1 indicates the placement and of electron donating and electron withdrawing groups on an electron conjugated system is important to increasing polarizability. Further, Table 1 structures are indicative of conjugated ring systems that may be further modified to enhance polarizability. However, they are non-limiting examples, and require additional resistive substituents (tails) to achieve high resistivity.

In another embodiment of the present disclosure, at least one tail-substituent is independently selected from the list comprising —$(CH_2)_nCH_3$, —$CH((CH_2)_nCH_3)_2$) (where n≥1), alkyl, aryl, substituted alkyl, substituted aryl, branched alkyl, branched aryl, complex cyclic alkyl groups, —X=CH(CH2)nCH3, —CC(CH2)nCH3, —X=C((CH2)nCH3)((CH2)mCH3) and any combination thereof and wherein the alkyl group is selected from methyl, ethyl, propyl, butyl, i-butyl and t-butyl groups, and the aryl group is selected from phenyl, benzyl and naphthyl groups where X is C, S, or N and n and m are independently selected from 1-20. In yet another embodiment of the present disclosure, the copolymers are selected from YanLi materials having following structures 1 to 26 as shown in Table 2 below.

TABLE 2

Examples of the Yan Li materials

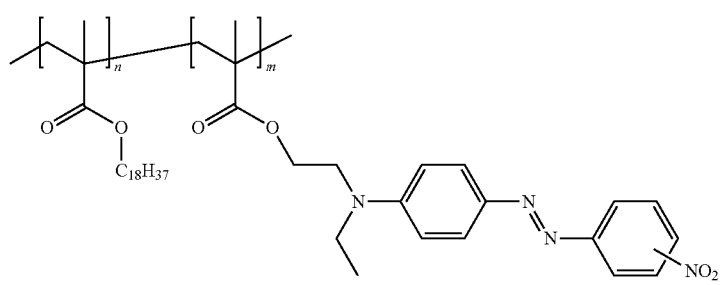

1

TABLE 2-continued
Examples of the Yan Li materials
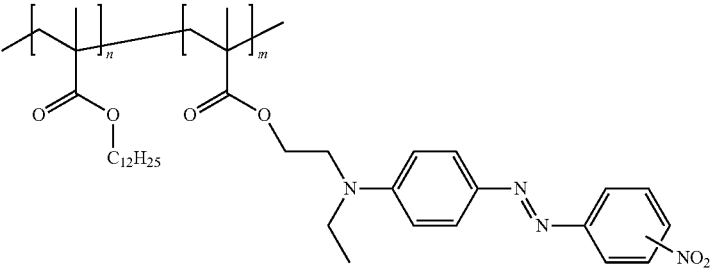
2
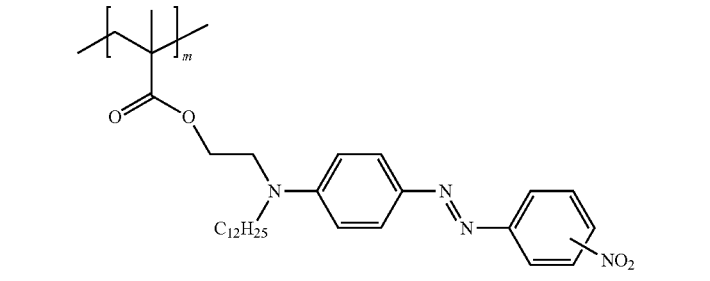
3
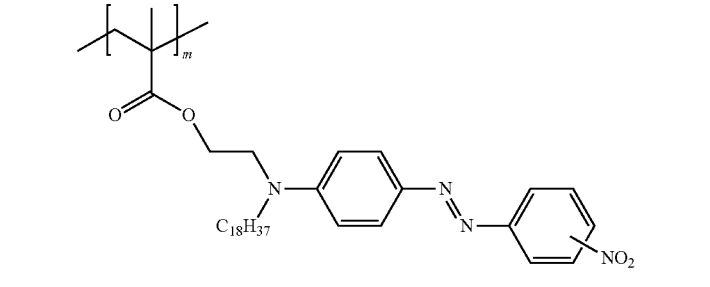
4
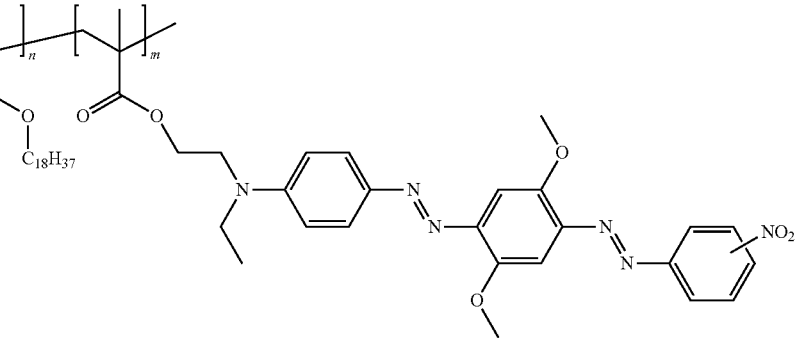
5
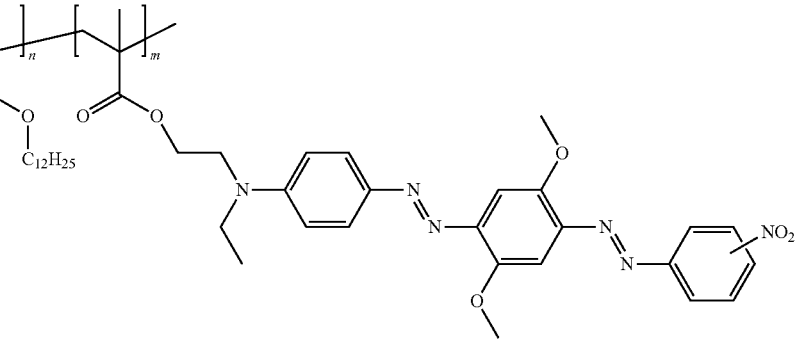
6

TABLE 2-continued
Examples of the Yan Li materials
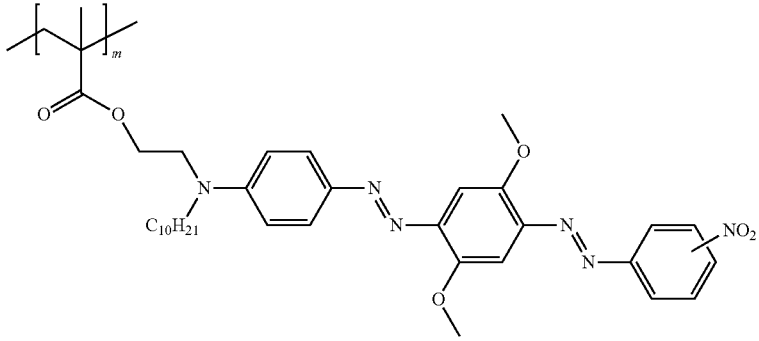
7
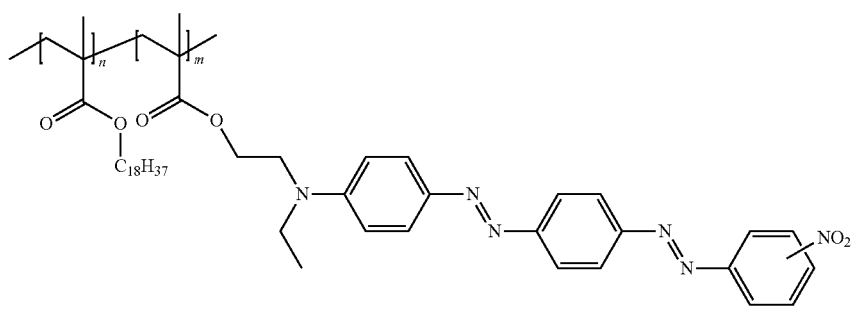
8
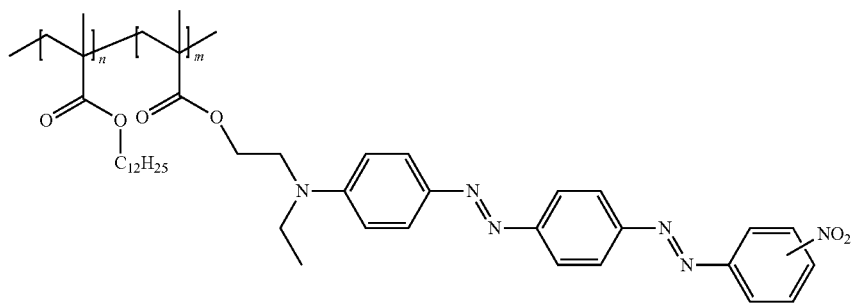
9
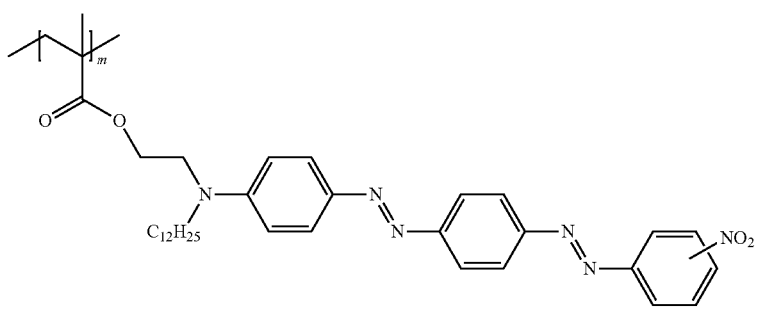
10
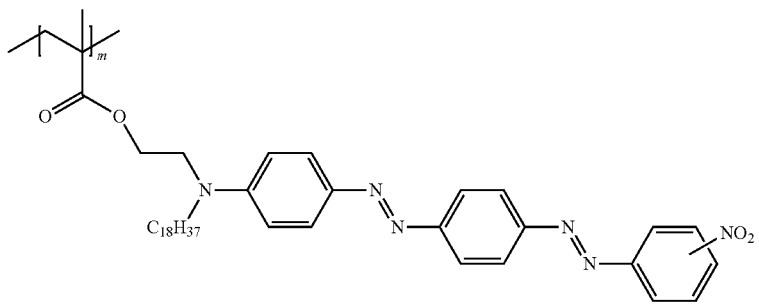
11

TABLE 2-continued
Examples of the Yan Li materials
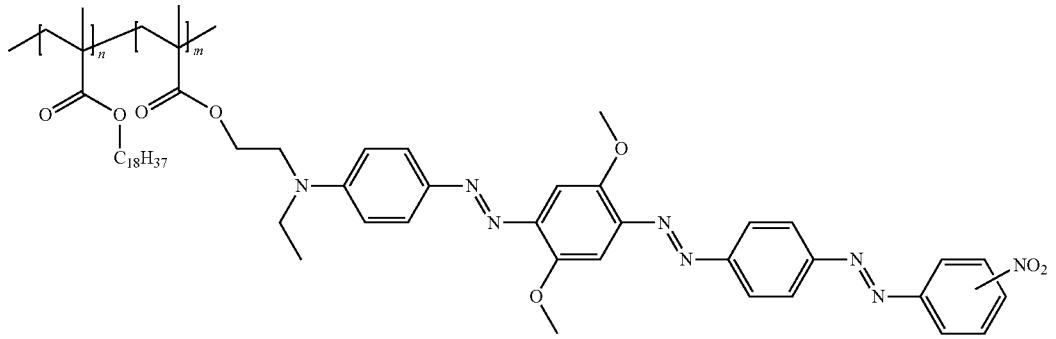
12
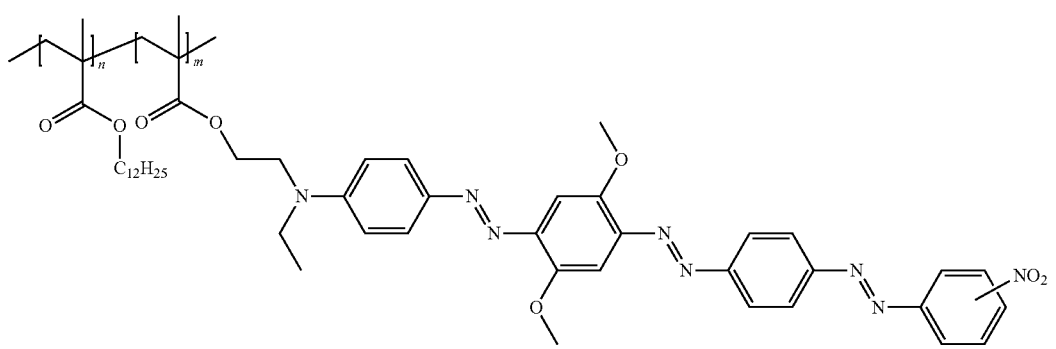
13
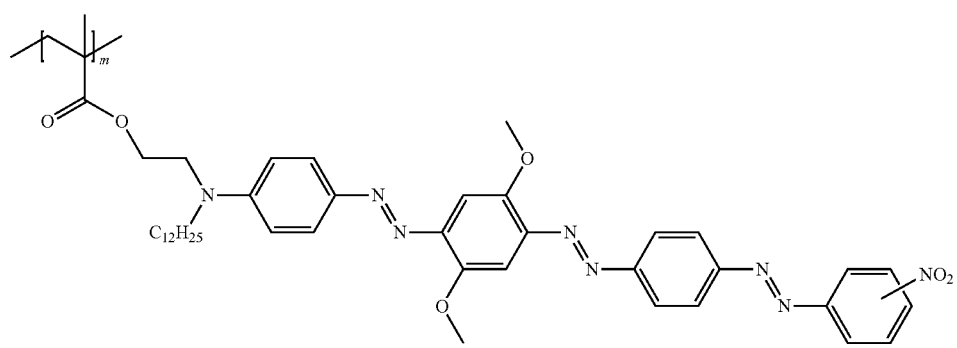
14
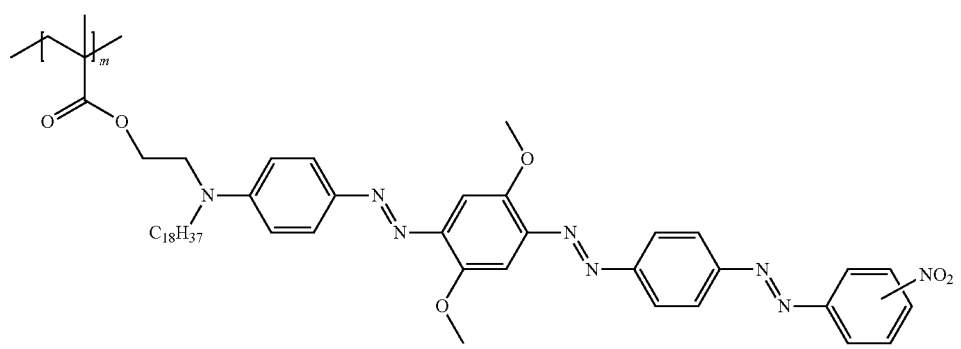
15

TABLE 2-continued
Examples of the Yan Li materials
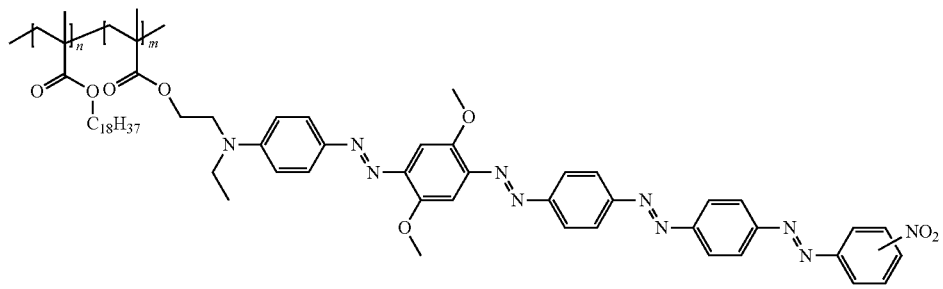
16
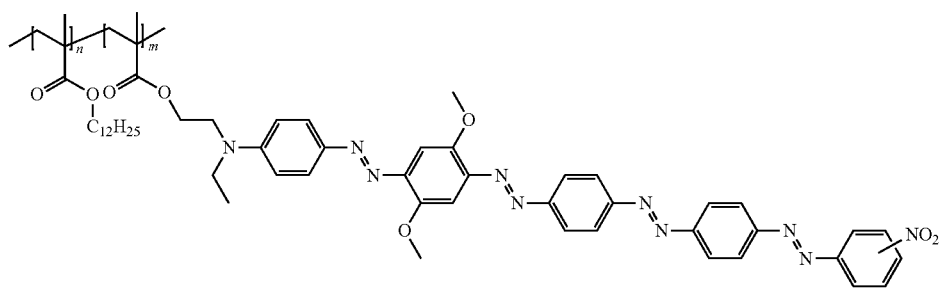
17
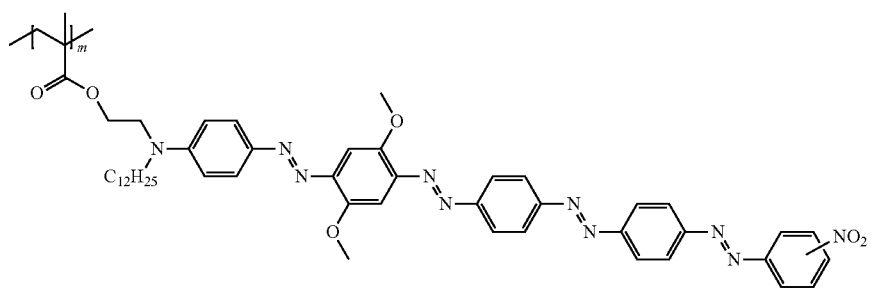
18
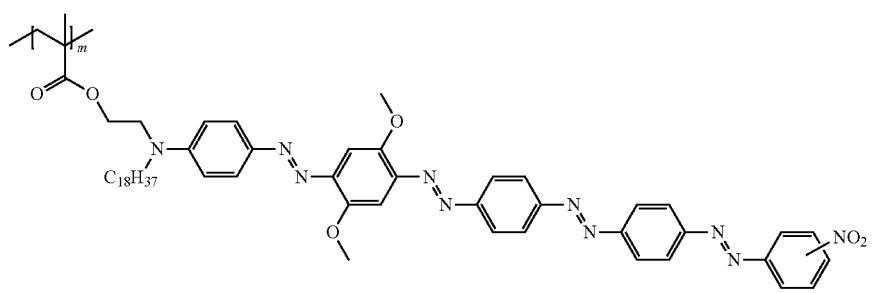
19

TABLE 2-continued
Examples of the Yan Li materials
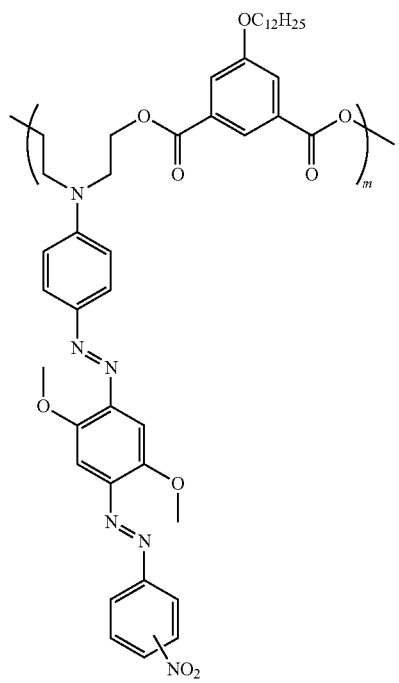
20
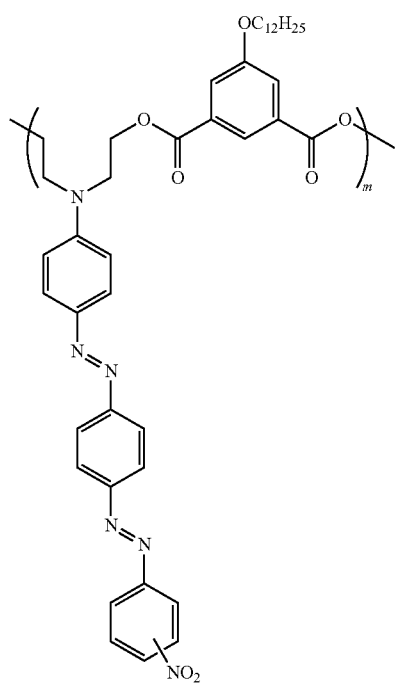
21

TABLE 2-continued
Examples of the Yan Li materials
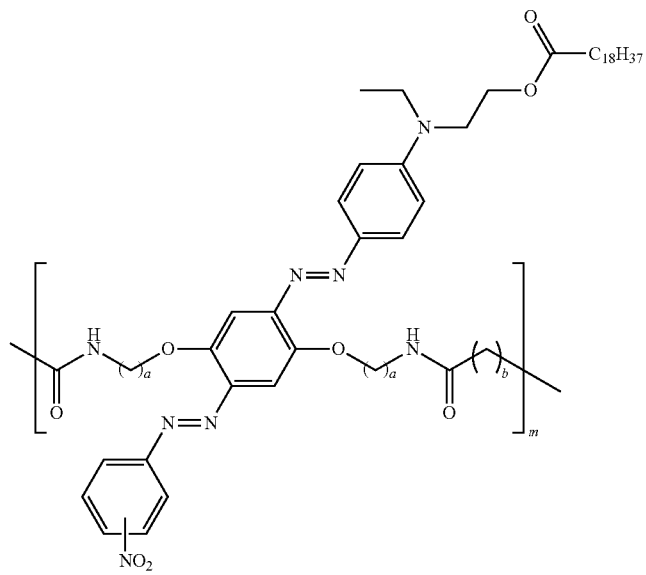
22
a = 2, b = 4
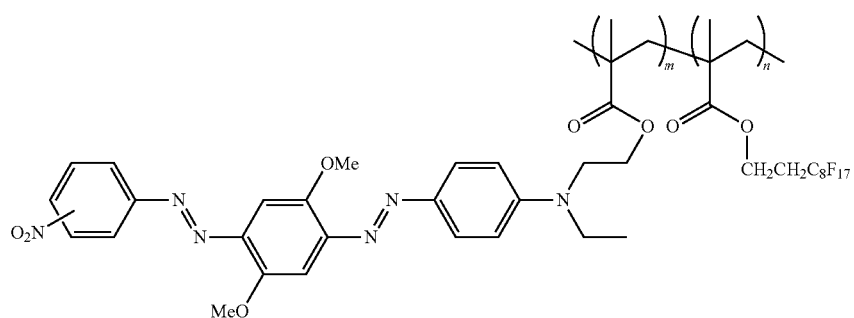
23
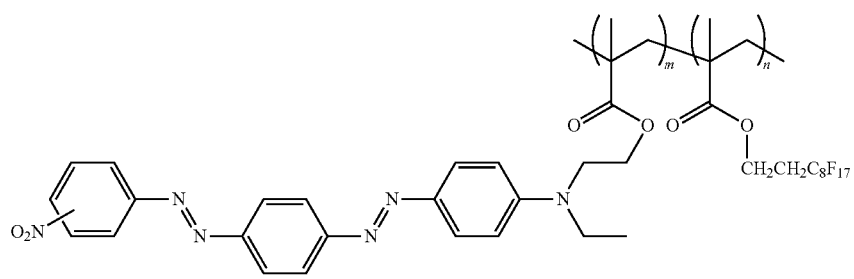
24
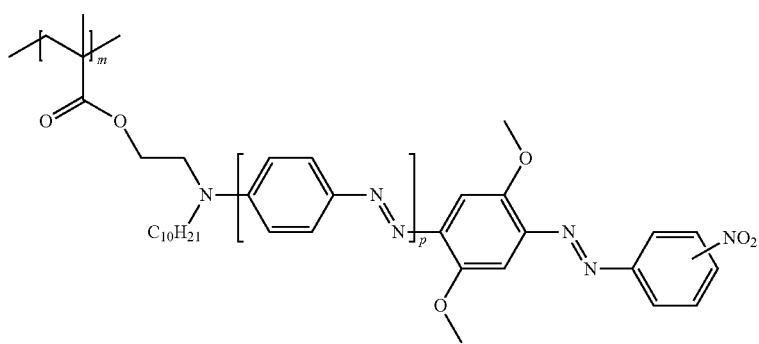
25
p = 2, 3, 4

TABLE 2-continued

Examples of the Yan Li materials

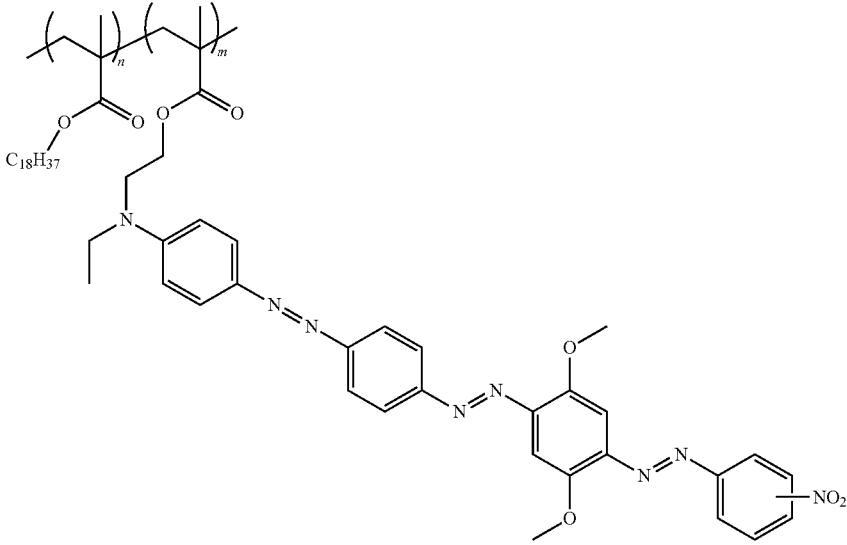

26

In one embodiment of the disclosed non-linear capacitor, the voltage $V_{int}$ aspires to the maximum voltage $V_{max}$ when the derivative $$\left.\frac{dQ}{dV}\right|_{V_{max}}$$

is increased. In another embodiment of the disclosed non-linear capacitor, the ratio $(V_{max}-V_{int})/V_{max}$ is less than 0.1. In yet another embodiment of the disclosed non-linear capacitor, the voltage V applied to the electrodes is approximately constant and is changed in a range between the voltage $V_{int}$ and the voltage $V_{max}$ during charging/discharging of the non-linear capacitor until (while) the charge Q on the electrodes is changed in a range between the charge $Q_{int}=Q(V_{int})$ and the maximum charge $Q_{max}=Q(V_{max})$. In another embodiment of the disclosed non-linear capacitor, the organic compound is characterized by an induced polarization $P_{ind}$ which may be written down in the form of decomposition into a series on degrees of intensity of a local electric field $E_{loc}$:

$$P_{ind} = \alpha \cdot E_{loc} + \beta \cdot E_{loc}^2 + \ldots ,$$

where α-linear polarizability, β-square polarizability.

The present disclosure provides the energy storage device as disclosed above.

In order that the invention may be more readily understood, reference is made to the following Figures, which are intended to be illustrative of the present disclosure, but is not intended to be limiting in scope.

FIG. 1 schematically shows a relation between a charge $Q=C(V)\cdot V$ on the electrodes of the capacitor and a voltage V applied to the electrodes (see, a curve A). The charge Q is non-linearly dependent on the voltage V according to the following monotonously increasing polynomial dependence $Q(V)=(C_0+\Sigma_{i=1}^m C_i V^i)\cdot V$, when the voltage V satisfies following inequality $0<V\leq V_{max}$, where the voltage $V_{max}$ is the maximum working voltage that does not exceed breakdown voltage $V_{bd}$ and which is selected out of security reasons, the coefficients $Q_i$ characterize the nonlinearity of the charge Q of the i-th order, m=1, 2, 3, 4, 5, or 6, and $Q_{11}=Q(V_{max})$. The straight line 2 is a tangent to the nonlinear dependence Q (V) when the voltage V is equal to the maximum voltage, i. e. $V=V_{max}$. This straight line B crosses the abscissa at the point $V=V_{int}$ and the charge corresponding to this voltage is equal to $Q_{int}=Q(V_{int})$. The following ratio is carried out for the difference between two voltages $V_{max}$ and $V_{int}$:

$$V_{max} - V_{int} = \frac{Q(V_{max})}{\left.\frac{dQ}{dV}\right|_{V_{max}}}.$$

It follows from the above expression that the difference $V_{max}-V_{int}$ is decreased with increasing of steepness of the nonlinear dependence at the maximum voltage $V_{max}$. During charging/discharging of the capacitor the voltage V changes in an interval between $V_{max}$ and $V_{int}$ while the charge Q changes between $Q_{max}$ and $Q_{int}$.

The present disclosure provides the non-linear capacitor comprising two metal electrodes positioned parallel to each other and which can be rolled or flat and planar and dielectric layer between this electrodes. The dielectric layer comprises at least one organic compound selected from copolymer, homo-polymer, Sharp polymers, NLSD compounds and combination thereof which have at least one electro-polarizable aromatic polycyclic conjugated core as disclosed above.

Figure 2A:
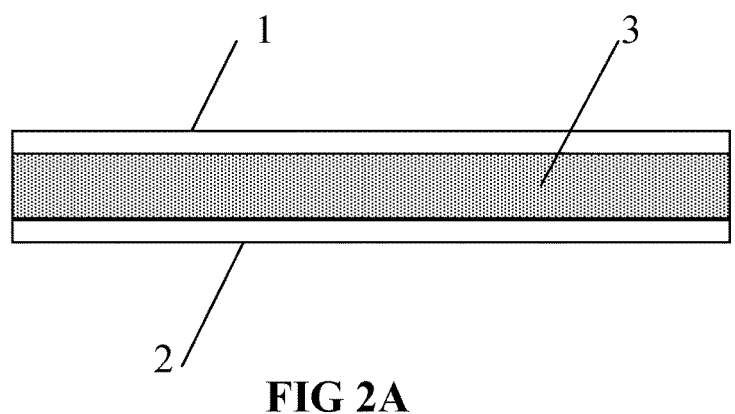
FIG. 2A schematically shows the disclosed capacitor with flat and planar electrodes.

The non-linear capacitor comprises a first electrode 1, a second electrode 2, and a dielectric layer 3 disposed between said first and second electrodes as shown in FIG. 2A. The electrodes 1 and 2 may be made of a metal, such as copper, zinc, or aluminum or other conductive material and are generally planar in shape.

The electrodes 1, 2 may be flat and planar and positioned parallel to each other. Alternatively, the electrodes may be planar and parallel, but not necessarily flat, they may be coiled, rolled, bent, folded, or otherwise shaped to reduce the overall form factor of the capacitor. It is also possible for the electrodes to be non-flat, non-planar, or non-parallel or some combination of two or more of these. By way of example and not by way of limitation, a spacing d between the electrodes 1, 2 may range from about 100 nm to about 10 000 μm. The maximum voltage $V_{bd}$ between the electrodes 1, 2 is approximately the product of the breakdown field $E_{bd}$ and the electrode spacing d. If $E_{bd}$=0.1 V/nm and the spacing d between the electrodes 1 and 2 is 10,000 microns (100,000 nm), the maximum voltage $V_{bd}$ would be 100,000 volts.

The electrodes 1, 2 may have the same shape as each other, the same dimensions, and the same area A. By way of example, and not by way of limitation, the area A of each electrode 1, 2 may range from about 0.01 m$^2$ to about 1000 m$^2$. These ranges are non-limiting. Other ranges of the electrode spacing d and area A are within the scope of the aspects of the present disclosure.

Figure 2B:
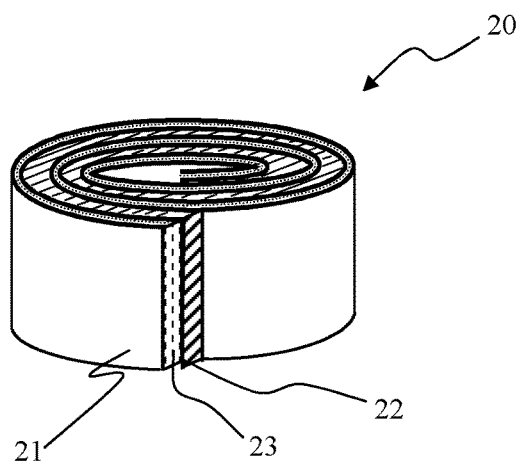
FIG. 2B schematically shows the disclosed capacitor with rolled (circular) electrodes.

The present disclosure include non-linear capacitors that are coiled, e.g., as depicted in FIG. 2B. In this example, a capacitor 20 comprises a first electrode 21, a second electrode 22, and a dielectric material layer 23 of the type described hereinabove disposed between said first and second electrodes. The electrodes 21, 22 may be made of a metal, such as copper, zinc, or aluminum or other conductive material and are generally planar in shape. In one implementation, the electrodes and dielectric material layer 23 are in the form of long strips of material that are sandwiched together and wound into a coil along with an insulating material, e.g., a plastic film such as polypropylene or polyester to prevent electrical shorting between the electrodes 21, 22.

Figure 3:
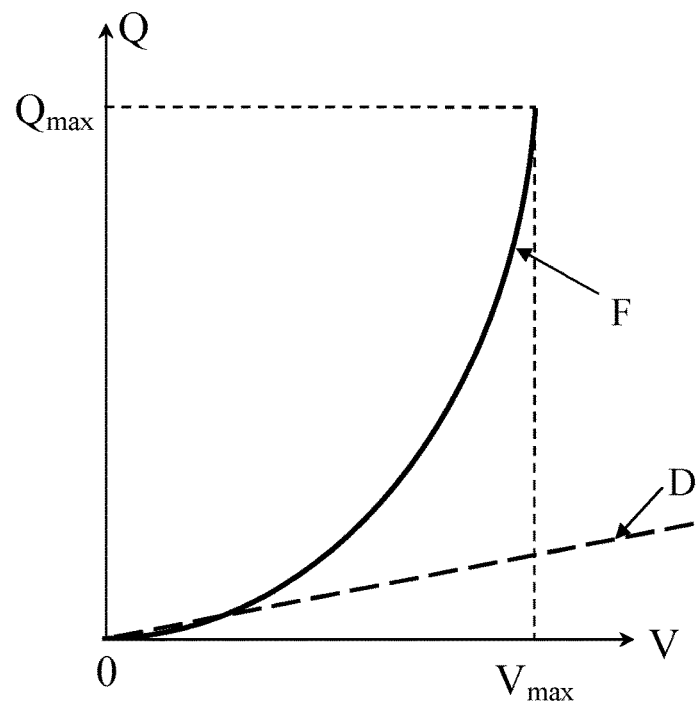
FIG. 3 schematically shows how the charge Q on the electrodes of a capacitor depends on the voltage applied to the electrodes of the nonlinear capacitor (F) and linear capacitor (D).

FIG. 3 schematically illustrates dependence of the charge (Q) accumulated on electrodes on the voltage (V) enclosed to the device (Q-V plot) for a standard material (D) and a material of the dielectric layer having at least one organic compound selected from copolymer, homo-polymer, Sharp polymers, NLSD compounds and combination thereof which have at least one electro-polarizable aromatic polycyclic conjugated core (F).

With reference to FIG. 3, the total energy stored in an exemplary device can depend on, for example, (a) the maximum attainable voltage across the device electrodes, $V_{max}$, (b) the charge stored on the device electrodes at this voltage, $Q_{max}$ and/or (c) the form of the Q-V curve for the device. Generally, the energy total stored in the device, E, is given by Equation (I):

$$E = \int_0^{Q_{max}} V(Q)dQ \qquad (I)$$

Without limitation, the energy stored in devices (and energy density) may be increased in at least the following three ways: increase of the breakdown voltage, increase of permittivity c of dielectric material of the metadielectric layer, and increase of an area under the Q-V curve.

The maximum voltage $V_{max}$ can be limited by the maximum voltage that can be sustained by a device, i.e., the breakdown voltage, $V_{bd}$. Devices designed to increase $V_{max}$ can allow increased breakdown voltage, $V_{bd}$.

Generally the energy stored in a device equals the area under the Q-V curve in a plot such as that shown in FIG. 3. For most materials the capacitance does not depend on Q (i.e., V(Q)=Q/C as indicated by dotted line "D" in FIG. 3) and the energy stored in the device is given by Equation (II):

$$E = \frac{1}{2} C^* V_{max}^2 \qquad (II).$$

If C is dependent on Q the form of the curve in FIG. 3 may allow an increased stored energy up to $C^*V_{max}^2$, which is two times the stored energy for most materials.

The area under the Q-V curve may be increased by including a dielectric material with non-linear dependence of permittivity on V.

Figure 4:
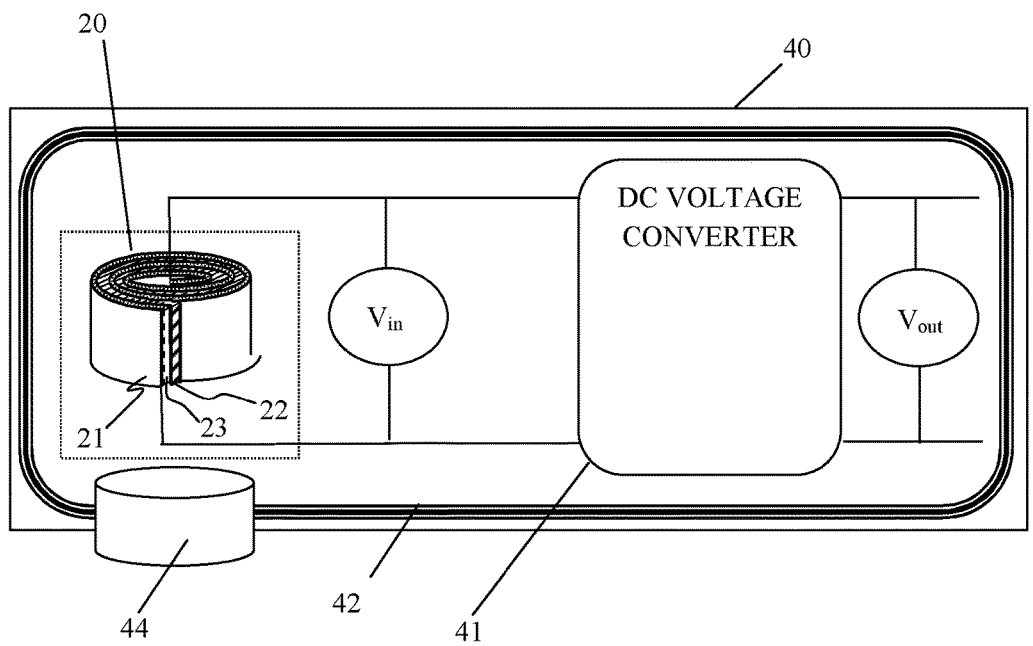
FIG. 4 schematically shows an energy storage cell utilizing an energy storage device according to aspects of the present disclosure.

One or more capacitors of the type shown in FIG. 2A or FIG. 2B may be used in an energy storage cell. By way of example, and not by way of limitation, FIG. 4 a possible implementation of an energy storage cell 40 that includes a capacitive energy storage device, e.g., one or more capacitors 20 of the type shown in FIG. 2B coupled to a DC voltage conversion device 41. Although a single meta-capacitor is depicted for simplicity, in other implementations the capacitive energy storage cell 40 combinations of two, or three or more meta-capacitors in a capacitor network involving various series and and/or parallel combinations may be coupled to the voltage conversion device 41.

In still another implementation, the capacitive energy storage cell 40 may further include a cooling system 42. In some implementations, the cooling can be passive, e.g., using radiative cooling fins on the capacitive energy storage device 40 and DC-voltage conversion device 41. Alternatively, a fluid such as air, water or ethylene glycol can be used as a coolant in an active cooling system. By way of example, and not by way of limitation, the cooling system 30 may include conduits in thermal contact with the capacitive energy storage device 20 and DC-voltage conversion device 41. The conduits are filled with a heat exchange medium, which may be a solid, liquid or gas. In some implementations, the cooling mechanism may include a heat exchanger 44 configured to extract heat from the heat exchange medium. In other implementations, the cooling mechanism 41 may include conduits in the form of cooling fins on the capacitive energy storage device 20 and DC-voltage conversion device 41 and the heat exchange medium is air that is blown over the cooling fins, e.g., by a fan. In another embodiment of the present invention, the heat exchanger 44 may include a phase-change heat pipe configured to carry out cooling. The cooling carried out by the phase-change heat pipe may involve a solid to liquid phase change (e.g., using melting of ice or other solid) or liquid to gas phase change (e.g., by evaporation of water or alcohol) of a phase change material. In yet another implementation, the conduits or heat exchanger 44 may include a reservoir containing a solid to liquid phase change material, such as paraffin wax.

Figure 5:
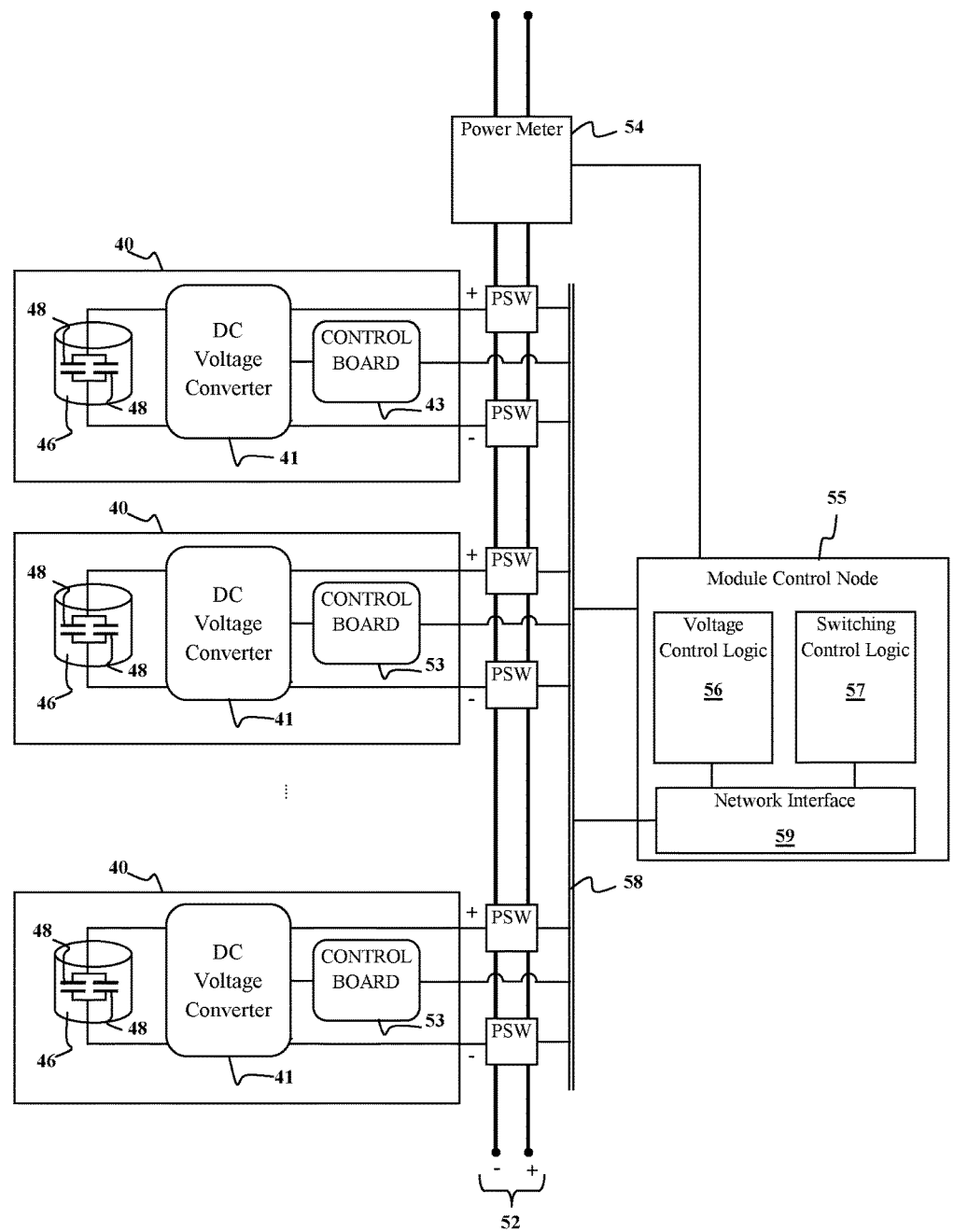
FIG. 5 shows an example of a capacitive energy storage module having two or more networked energy storage cells according to an alternative aspect of the present disclosure.

As an aspect of the present disclosure, a capacitive energy storage module 50, e.g., as illustrated in FIG. 5. In the illustrated example, the energy storage module 50 includes two or more energy storage cells 40 of the type described above. Each energy storage cell includes a capacitive energy storage device 46 having one or more capacitors 48 and a DC-voltage converter 41, which may be a buck converter, boost converter, or buck/boost converter. In addition, each module may include a control board 49 containing suitable logic circuitry, e.g., microprocessor, microcontroller, application specific integrated circuit (ASIC), field programmable gate array (FPGA), a complex programmable logic device (CPLD), capable of implementing closed loop control processes and (optionally) a communication interface, as well as an analog to digital converter coupled to sensors on the DC-voltage conversion device 41, e.g., voltage sensors V for the input voltage $V_{in}$ and the output voltage $V_{out}$, current sensors A for current $I_{sd}$ to/from the capacitive energy storage device 46 and/or current Ivc to/from the DC-voltage conversion device 41, temperature sensors on the capacitive energy storage device and/or DC-voltage conversion device. In some implementations, the control board 49 may be integrated into the DC-voltage conversion device 41. The DC-voltage conversion device 41 may contain a buck regulator, a boost regulator, buck and boost regulators with separate input/outputs, a bidirectional boost/buck regulator, or a split-pi converter and the control board 49 may be configured to maintain a constant output voltage $V_{out}$ from the DC-voltage conversion device during discharge, and/or charge the capacitor at a more-or-less constant current while maintaining a stable input voltage. The DC-voltage conversion device 41 and the control board 49 may be configured to maintain the voltage in a desired range. By way of example, and not by way of limitation, the control board 49 may be based on a controller for a bidirectional buck/boost converter. In such a configuration, the control board 59 stabilizes the output voltage of the DC-voltage conversion device according to an algorithm forming a suitable control loop. One example of a possible control loop is described in U.S. Patent Application Publication Number 20170237271, which is incorporated herein by reference.

The specifics of operation of the control board 49 are somewhat dependent on the type of buck/boost converter(s) used in the DC-voltage conversion device 41. For example, a buck/boost converter may be a single switch converter having a high-side switch with an input side coupled to the input voltage $V_{in}$ and an output side coupled to one side of an inductor, the other side of which is connected to the ground or common voltage. A capacitor is coupled across the output voltage $V_{out}$. A pulsed switching signal turns the switch on and off. The output voltage depends on the duty cycle of the switching signal. By way of example, the switches may be implanted as gated switch devices, e.g., MOSFET devices, stacked MOSFET devices, IGCT devices, high drain-source voltage SiC MOSFET devices, and the like depending on the voltage and/or current requirements of the DC-voltage converter for the energy storage cell. In the case of gated switching devices, the control board provides the signals to the gate terminals of the switching devices. The control board 49 can configure this type of buck/boost converter to buck or boost by adjusting the duty cycle of the switching signal.

The module 50 may further include an interconnection system that connects the anodes and cathodes of the individual energy storage cells to create a common anode and common cathode of the capacitive energy storage module. In some implementations, the interconnection system may include a parameter bus 52 and power switches PSW. Each energy storage cell 40 in the module 50 may be coupled to the parameter bus 52 via the power switches PSW. These switches allow two or more modules to be selectively coupled in parallel or in series via two or more rails that can serve as the common anode and common cathode. The power switches can also allow one or more energy storage cells to be disconnected from the module, e.g., to allow for redundancy and/or maintenance of cells without interrupting operation of the module. The power switches PSW may be based on solid state power switching technology or may be implemented by electromechanical switches (e.g., relays) or some combination of the two.

In some implementations, the energy storage module 50 further comprises a power meter 54 to monitor power input or output to the module. In some implementations, the energy storage module further comprises a networked control node 55 configured to control power output from and power input to the module. The networked control node 55 allows each module to talk with a system control computer over a high speed network. The networked control node 55 includes voltage control logic circuitry 56 configured to selectively control the operation of each of voltage controller 41 in each of the energy storage cells 40, e.g., via their respective control boards 49. The control node 55 may also include switch control logic circuitry 57 configured to control operation of the power switches PSW. The control boards 49 and power switches PSW may be connected to the control node 55 via a data bus 58. The voltage control and switching logic circuitry in the networked control node 55 may be implemented by one or more microprocessors, microcontrollers, application specific integrated circuits (ASICs), field programmable gate arrays (FPGAs), or complex programmable logic devices (CPLDs). The control node 55 may include a network interface 59 to facilitate transfer of signals between the voltage control logic circuitry 57 and the control boards 49 on the individual energy storage cells 40 and also to transfer signals between the switching logic circuitry 56 and the power switches PSW, e.g., via the data bus 58.

Figure 6:
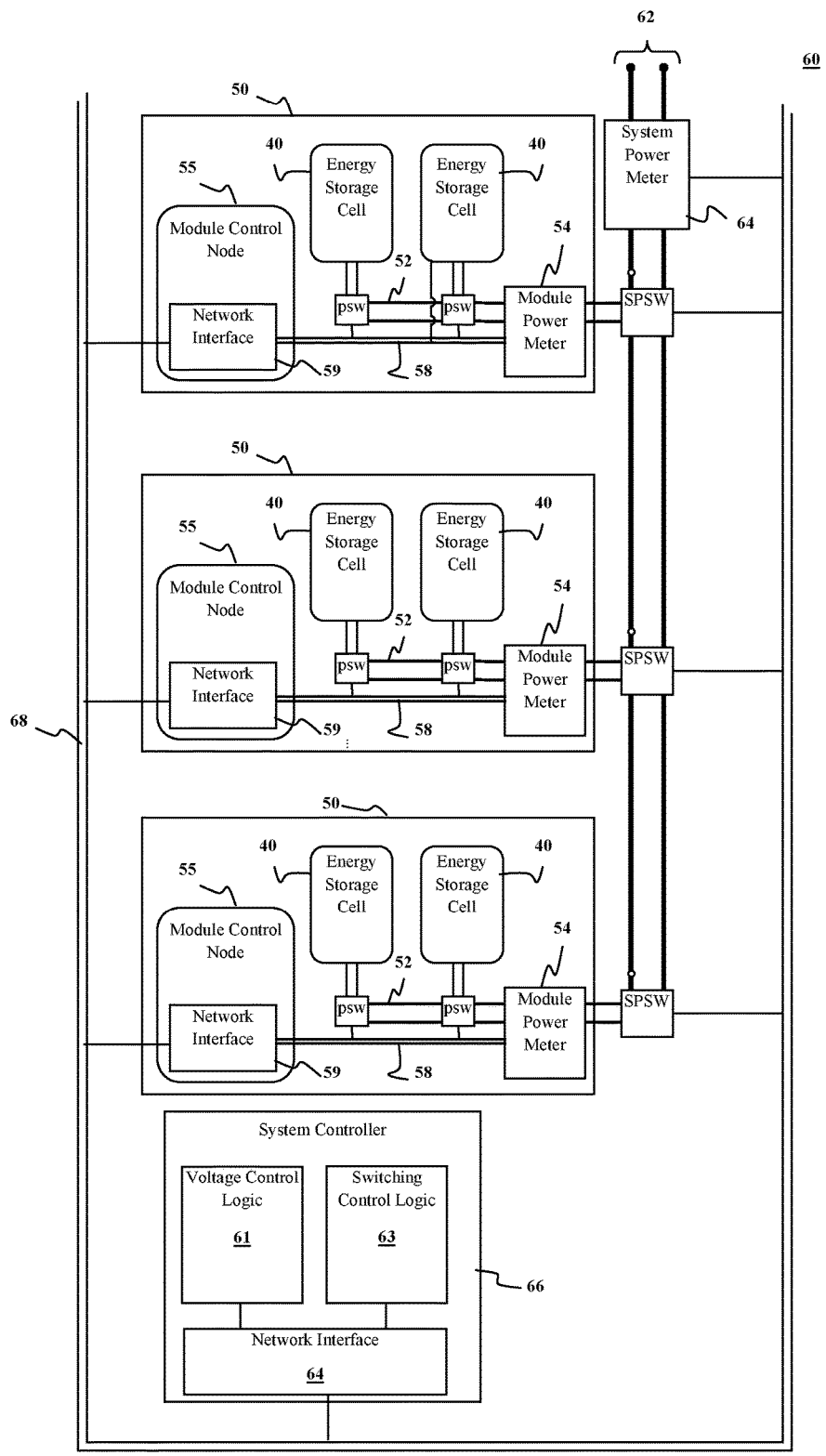
FIG. 6 shows an example of a capacitive energy storage system having two or more energy storage networked modules according to an alternative aspect of the present disclosure.

According to yet another aspect of the present disclosure a capacitive energy storage system may include two or more networked capacitive energy storage modules, e.g., of the type shown in FIG. 6. One embodiment of such a capacitive energy storage system 60 is shown in FIG. 6. The system 60 includes two or more energy storage modules 50 of the type shown in FIG. 5. Each capacitive energy storage module 50 includes two or more capacitive energy storage cells 40, e.g., of the type shown in FIG. 4 connected by an interconnection system 52 and controlled by a control node 55. Each capacitive energy storage module may also include a module power meter 54. Although it is not shown in FIG. 6, each control node 55 may include voltage control logic circuitry 56 to control voltage controllers within the individual capacitive energy storage cells 40 and switching logic circuitry 57 to control internal power switches with the module, as described above. In addition, each control node 55 includes an internal data bus 58 and a network interface 59, which may be configured and connected as described above. Power to and from capacitive energy storage modules 50 is coupled to a system power bus 62 via system power switches SPSW, which may be based on solid state power switching technology or may be implemented by electromechanical switches (e.g., relays) or some combination of the two. In some implementations, there may be an inverter (not shown) coupled between each capacitive energy storage module 50 and the system power bus 62 to convert DC power from the module to AC power or vice versa.

The system 60 includes a system controller 66 connected to a system data bus 68. The system controller may include switching control logic 63, voltage control logic 61, and system network interface 64. The voltage control logic 60 may be configured to control the operation of individual DC-voltage controllers within individual cells 40 of individual modules 50. The switching control logic 63 may be configured to control operation of the system power switches SPSW and also the power switches PSW within individual capacitive energy storage modules 50. Voltage control signals may be sent from the voltage control logic 63 to a specific DC-voltage control device 41 within a specific capacitive energy storage cell 40 of a specific capacitive energy storage module through the network interface 64, the system data bus 68, the module network interface 69 of the control node 46 for the specific module, the module data bus 68, and the control board 59 of the individual cells 50.

By way of example, and not by way of limitation, the system controller 66 may be a deterministic controller, an asynchronous controller, or a controller having distributed clock. In one particular embodiment of the capacitive energy storage system 60, the system controller 66 may include a distributed clock configured to synchronize several independent voltage conversion devices in one or more capacitive energy storage cells of one or more of the capacitive energy storage modules 50.

Aspects of the present disclosure allow for electrical energy storage on a much larger scale than possible with conventional electrical energy storage systems. A wide range of energy storage needs can be met by selectively combining one or more capacitors with a DC-voltage conversion devices into a cell, combining two or more cells into a module, or combining two or more modules into systems.

Although the present invention has been described in detail with reference to a particular preferred embodiment, persons possessing ordinary skill in the art to which this invention pertains will appreciate that various modifications and enhancements may be made without departing from the spirit and scope of the claims that follow. Any feature, whether preferred or not may be combined with any other feature whether preferred or not. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A non-linear capacitor comprising
a first electrode,
a second electrode, and
a dielectric layer disposed between said first and second electrodes,
wherein the dielectric layer comprises at least one organic compound selected from copolymer, homo-polymer, Sharp polymers, NLSD compounds and combination thereof which have at least one electro-polarizable aromatic polycyclic conjugated core,
wherein a relationship between a capacity C of the capacitor and a voltage V between the first and second electrodes is characterized by a monotonically increasing polynomial dependence $C_0+\Sigma_{i=1}^{m} C_i V^i$, when the voltage V satisfies by following inequality $0<V \leq V_{max}$, where the voltage $V_{max}$ is the maximum working voltage that does not exceed breakdown voltage $V_{bd}$ and which is selected out of safety reasons, where at least one coefficient $C_i$ is not equal to 0 when the index i ranges from 2 to m, and m=2, 3, 4, 5, or 6.

2. The non-linear capacitor according to claim 1, wherein a working range of voltage is from $V_{int}$ to $V_{max}$ where $V_{int}$ is determined by the intersection the straight line that is tangent to the dependence $Q(V)=C(V) \cdot V$ at the point $V=V_{max}$ with the abscissa axis, and the difference between voltages $V_{max}$ and $V_{int}$ is defined by the following ratio:

$$V_{max} - V_{int} = \frac{Q(V_{max})}{\frac{dQ}{dV}\bigg|_{V_{max}}}$$

3. The non-linear capacitor according to claim 1, wherein the electro-polarizable aromatic polycyclic conjugated cores interact with each other due to dipole and π-π interactions and form molecular stacks, and the organic compound further comprises alkyl tail-substituents which are bonded to the polymer backbone or to conjugated Sharp and NLSD molecular compounds, wherein the alkyl tail-substitutes interact with each other due to hydrophobic interaction and also form isolating cover round the molecular stacks, provide solubility of the organic compound, and preclude an avalanche breakdown of the dielectric layer at the working voltage applied to the electrodes of the capacitor.

4. The non-linear capacitor according to claim 1, wherein the electro-polarizable aromatic polycyclic conjugated core comprises benzene rings bonded with linker groups and is described by following structure formula:

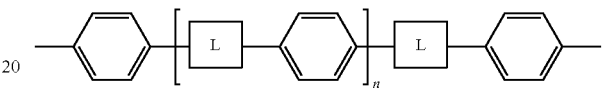

where L is linker group which is selected from —N=N—, —CC— (alkyl/and —CH=CH— and n=0, 1, 2, 3, 4, 5, and 6.

5. The non-linear capacitor according to claim 1, wherein the electro-polarizable aromatic polycyclic conjugated core further comprises electrophilic groups (acceptors) and/or nucleophilic groups (donors) located in apex positions and/or in side (lateral) positions.

6. The non-linear capacitor according to claim 5, wherein the electrophilic groups (acceptors) are selected from —$NO_2$, —$NH_3^+$ and —NRR'R" (quaternary nitrogen salts), counterion Cl⁻ or Br⁻, —CHO (aldehyde), —CRO (keto group), —$SO_3H$ (sulfonic acids), —$SO_3R$ (sulfonates), $SO_2NH_2$ (sulfonamides), —COOH (carboxylic acid), —COOR (esters, from carboxylic acid side), —COCl (carboxylic acid chlorides), —CONH2 (amides, from carboxylic acid side), —$CF_3$, —$CCl_3$, —CN, wherein R is radical selected from the list comprising alkyl (methyl, ethyl, isopropyl, tert-butyl, neopentyl, cyclohexyl etc.), allyl (—CH2-CH=CH2), benzyl (—CH2C6H5) groups, phenyl (+substituted phenyl) and other aryl (aromatic) groups and where R' & R" are independently selected for list of R radicals.

7. The non-linear capacitor according to claim 5, wherein the nucleophilic groups (donors) are selected from —O⁻ (phenoxides, like —ONa or —OK), —$NH_2$, —NHR, $NR_2$, —OH, OR (ethers), —NHCOR (amides, from amine side), —OCOR (esters, from alcohol side), alkyls, —$C_6H_5$, vinyls, —NRR' wherein R and R' are radicals independently selected from the list comprising alkyl (methyl, ethyl, isopropyl, tert-butyl, neopentyl, cyclohexyl etc.), allyl (—CH2-CH=CH2), benzyl (—CH2C6H5) groups, phenyl (+substituted phenyl) and other aryl (aromatic) groups.

8. The non-linear capacitor according to claim 3, wherein at least one tail-substituent is independently selected from the list comprising —$(CH_2)_n CH_3$, —CH($(CH_2)_n CH_3)_2$) (where n≥1), alkyl, aryl, substituted alkyl, substituted aryl, branched alkyl, branched aryl, complex cyclic alkyl groups, —X=CH(CH2)nCH3, —CC(CH2)nCH3, —X=C((CH2)nCH3)((CH2)mCH3) and any combination thereof and wherein the alkyl group is selected from methyl, ethyl, propyl, butyl, i-butyl and t-butyl groups, and the aryl group is selected from phenyl, benzyl and naphthyl groups where X is C, S, or N and n and m are independently selected from 1-20.

9. The non-linear capacitor according to claim 1, wherein the copolymers are selected from YanLi materials having following structures 1 to 26:
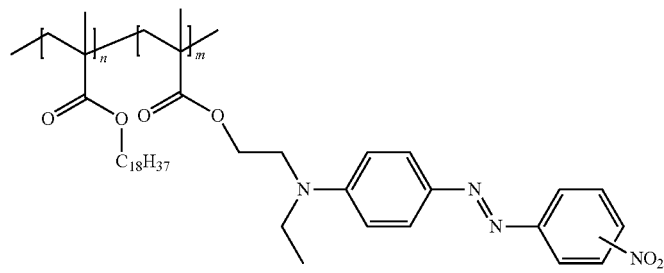
1
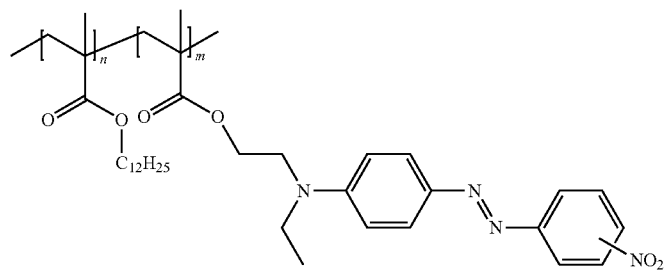
2
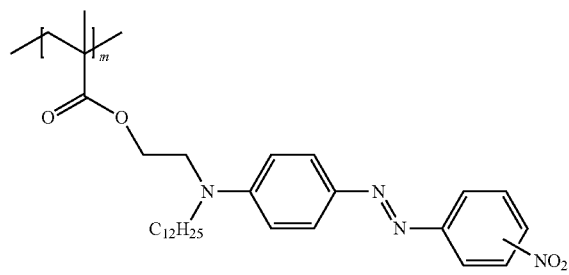
3
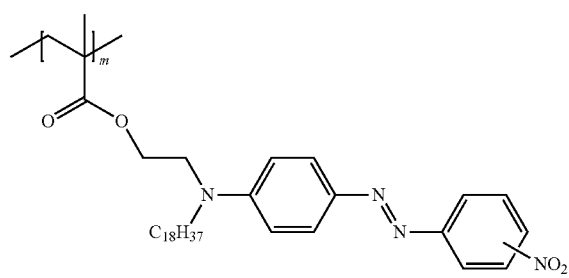
4
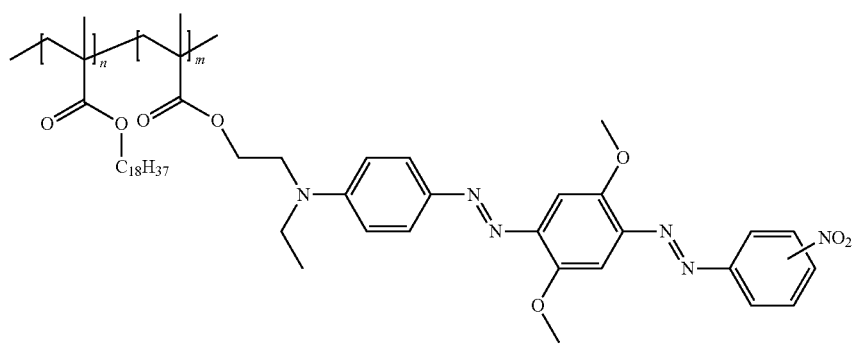
5

-continued
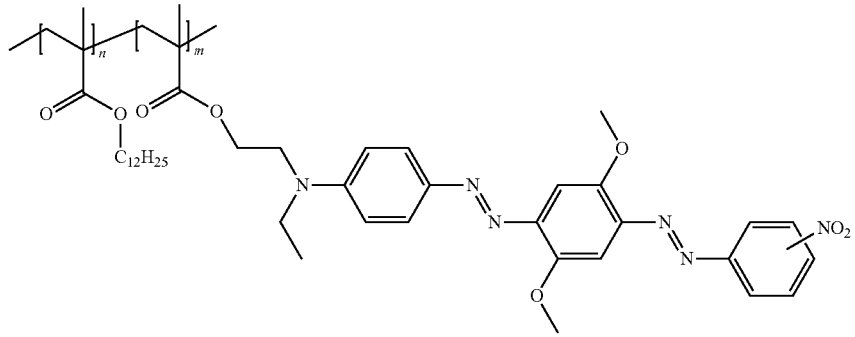
6
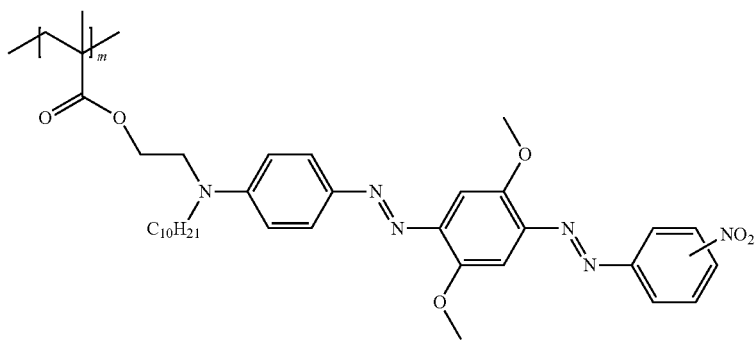
7
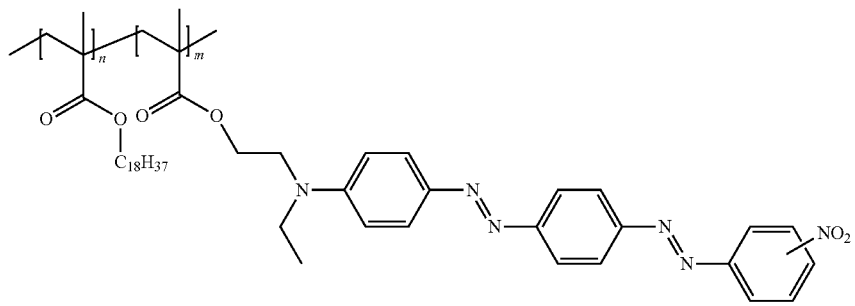
8
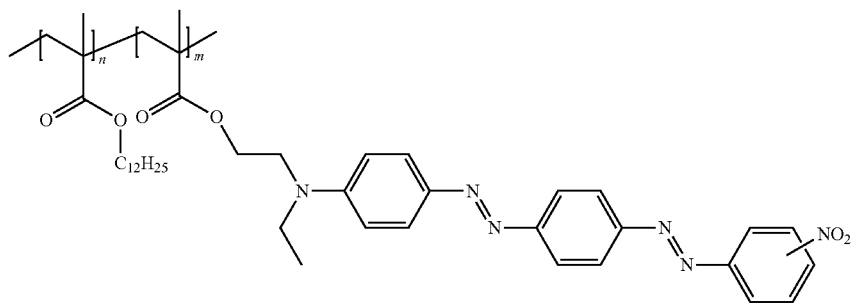
9
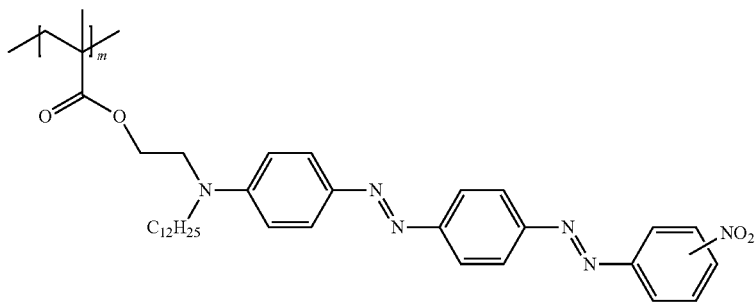
10

-continued
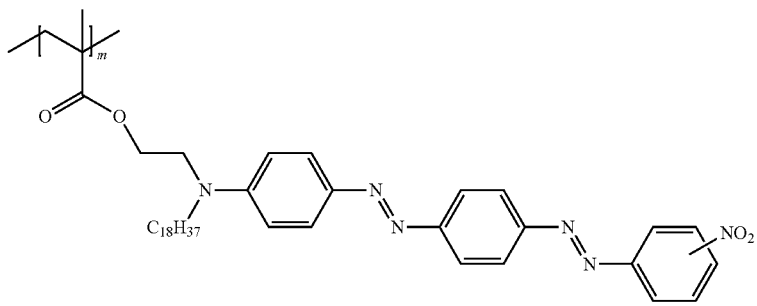
11
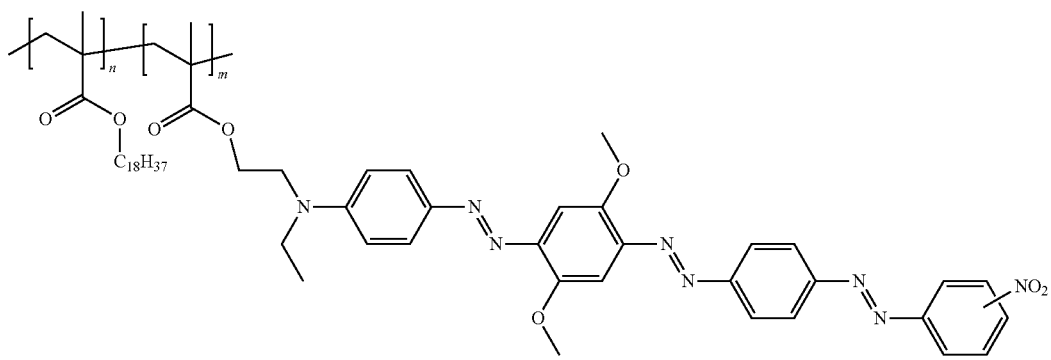
12
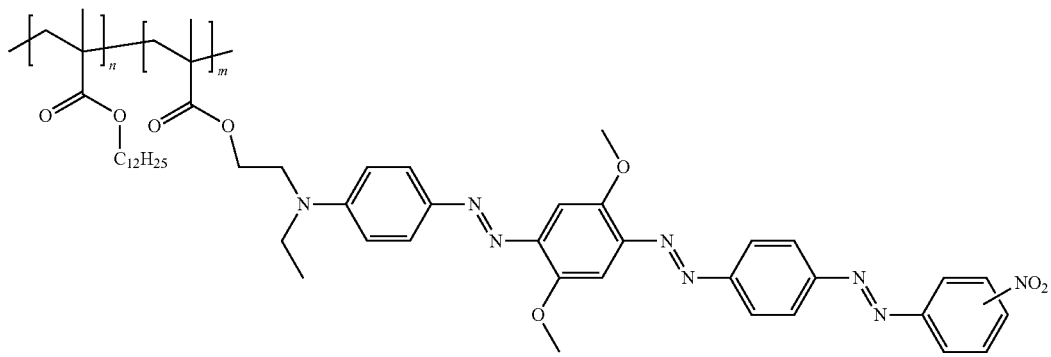
13
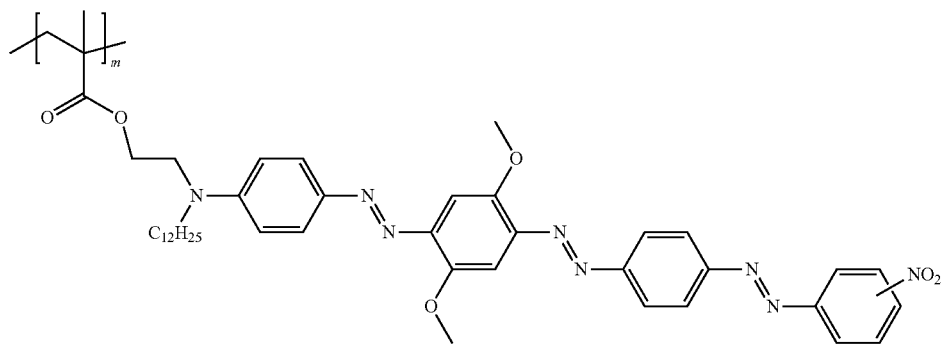
14

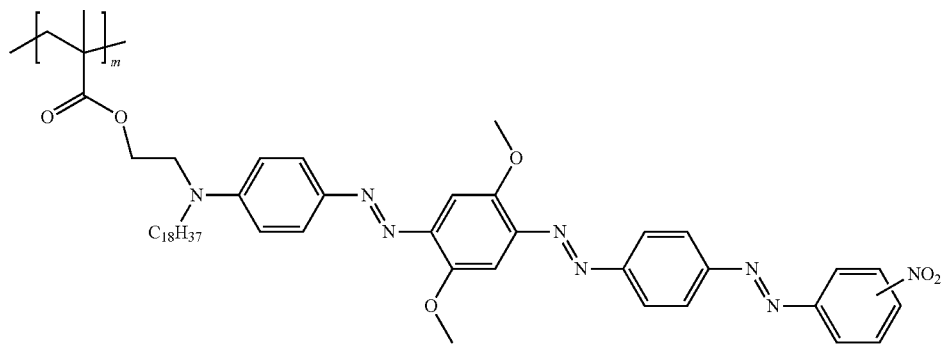
15
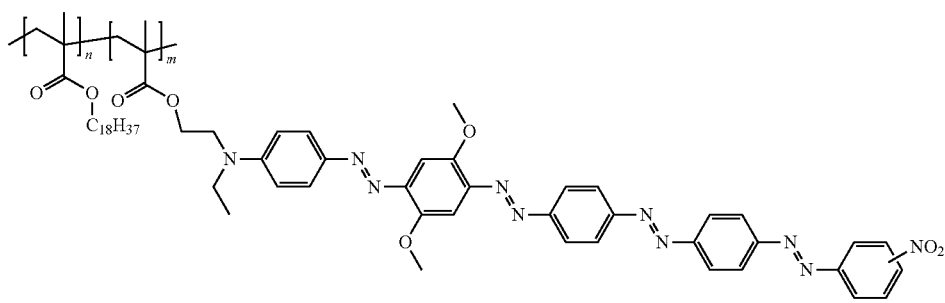
16
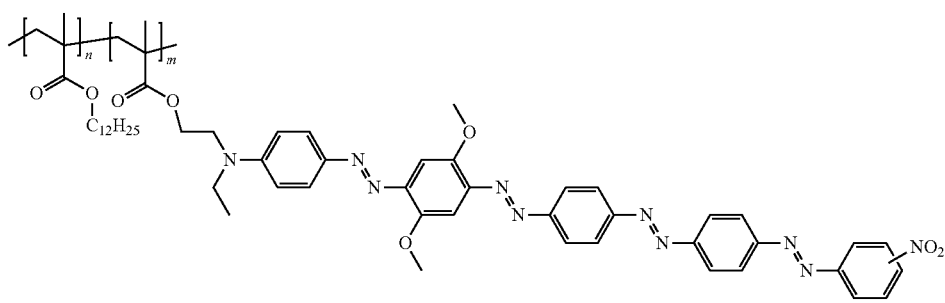
17
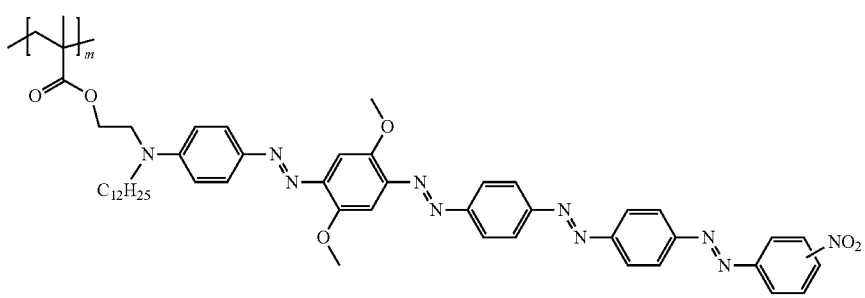
18
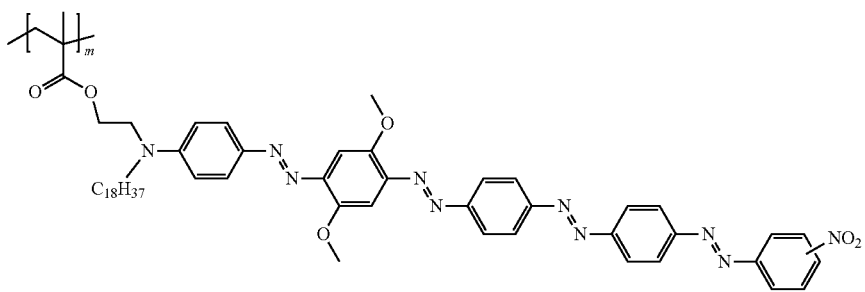
19

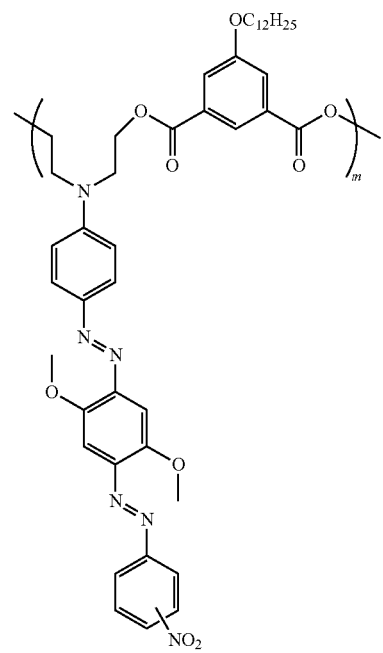
20
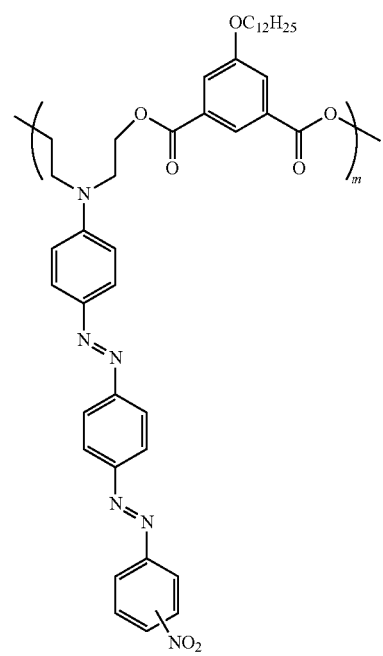
21

-continued
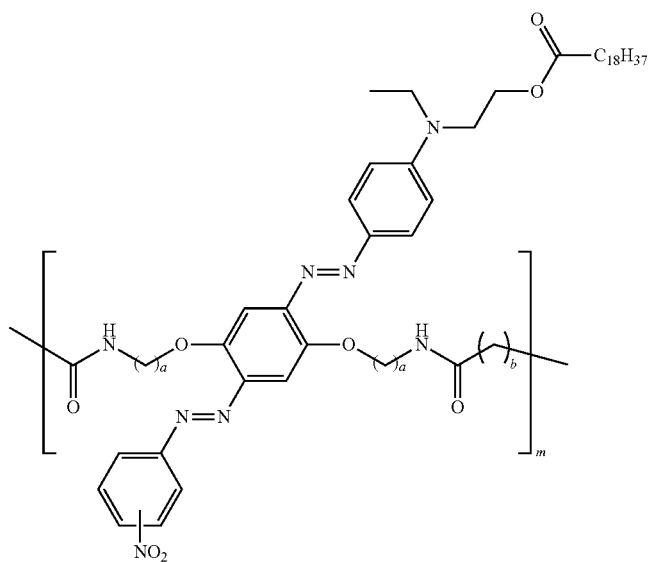
a = 2, b = 4
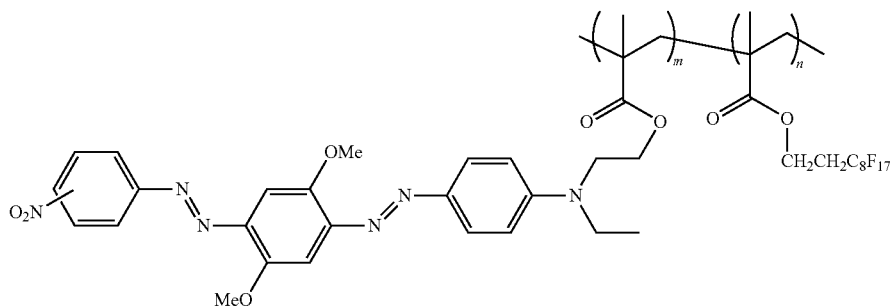
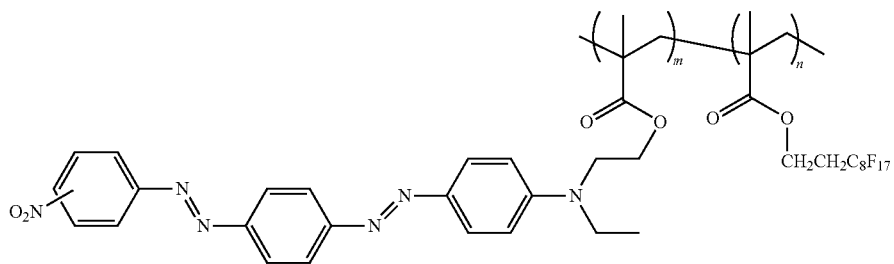
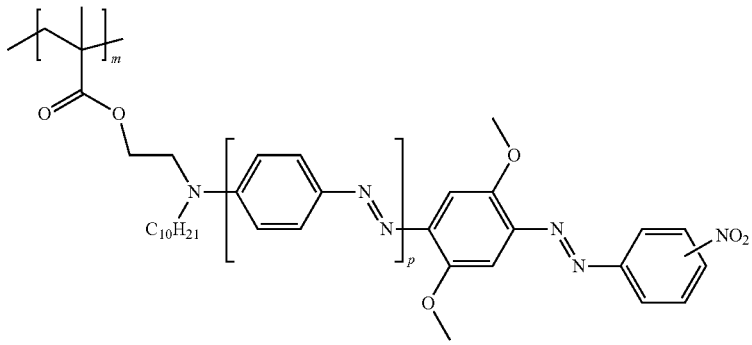
p = 2, 3, 4

-continued

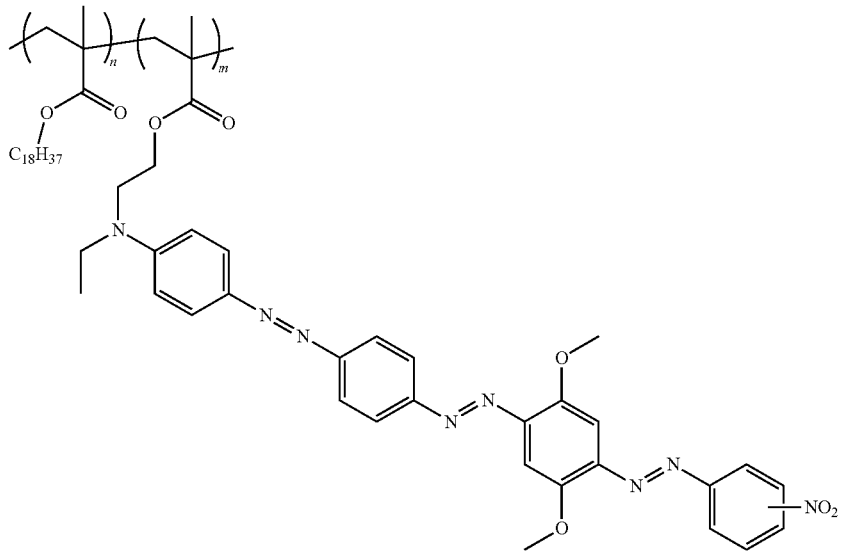

26.

10. The non-linear capacitor according to claim 2, wherein the voltage $V_{int}$ aspires to the maximum voltage $V_{max}$ when the derivative $$\left.\frac{dQ}{dV}\right|_{V_{max}}$$

is increased.

11. The non-linear capacitor according to claim 2, wherein the ratio $(V_{max}-V_{int})/V_{max}$ is less than 0.1.

12. The non-linear capacitor according to claim 2, wherein the voltage V applied to the electrodes is approximately constant and is changed in a range between the voltage $V_{int}$ and the voltage $V_{max}$ during charging/discharging of the capacitor until (while) the charge Q on the electrodes is changed in a range between the charge $Q_{int}=Q(V_{int})$ and the maximum charge $Q_{max}=Q(V_{max})$.

13. The non-linear capacitor according to claim 1, wherein the organic compound is characterized by an induced polarisation $P_{ind}$ approximated by a decomposition into a series on degrees of intensity of a local electric field $E_{loc}$:

$$P_{ind} = \alpha \cdot E_{loc} + \beta \cdot E_{loc}^2 + \dots ,$$

where $\alpha$ is a linear polarizability, $\beta$ is a square polarizability.

14. An energy storage device comprising the non-linear capacitor with a power-law dependence of capacitance on voltage according to claim 1, which uses a power electronics in a voltage range from $V_{max}$ 200 volts to $V_{max}$ 1000 volts.

15. An energy storage device comprising the non-linear capacitor with a power-law dependence of capacitance on voltage according to claim 1, which uses a power electronics and operates at a $V_{max}$ voltage greater than 1000 volts.

* * * * *